US006451759B1

(12) United States Patent
Kang et al.

(10) Patent No.: US 6,451,759 B1
(45) Date of Patent: Sep. 17, 2002

(54) NONCLEAVABLE FAS LIGAND

(75) Inventors: Sang-Mo Kang, San Francisco, CA (US); Andries Erik Braat, The Hague (NL); Steinunn Baekkeskov; Peter G. Stock, both of San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 316 days.

(21) Appl. No.: 09/006,755

(22) Filed: Jan. 14, 1998

(51) Int. Cl.[7] .......................... A61K 38/19; C07K 14/52

(52) U.S. Cl. .......................... 514/2; 530/350; 530/351; 435/320.1; 435/325; 435/365.1; 435/252.3; 435/254.11; 536/23.5; 536/23.1; 424/450

(58) Field of Search .......................... 424/450; 530/350, 530/351; 536/23.5, 23.1; 514/12; 435/320.1, 325, 365.1, 252.3, 254.11

(56) References Cited

U.S. PATENT DOCUMENTS

| 4,683,195 A | 7/1987 | Mullis et al. .................. 435/6 |
| 5,858,990 A | * 1/1999 | Walsh .......................... 514/44 |

FOREIGN PATENT DOCUMENTS

| EP | 0 675 200 A1 | 10/1995 |
| WO | WO 97/18307 | * 5/1997 |
| WO | WO98/21232 | 5/1998 |

OTHER PUBLICATIONS

Seino, et al., "Antitumor effect of locally produced CD95 ligand," Nature Medicine, vol. 3, Feb. 1997, pp. 165–170.
Abul K. Abbas, "Die and Let Live: Eliminating Dangerous Lymphocytes," Cell 84:655–657, Mar. 8, 1996.
Mark R. Alderson et al., "Fas Ligand Mediates Activation–Induced Cell Death in Human T Lymphocytes," J. Exp. Med. 181:71–77 (1995).
Ronald G. Almquist et al., "Synthesis and Biological Activity of a Ketomethylene Analogue of a Tripeptide Inhibitor of Angiotensin Converting Enzyme," J. Med Chem., 23:1392–1398 (1980).
Michael A. Barry et al., "Protection against mycoplasma infection using expression–library immunization," Nature 377:632–635 (1995).
Donald Bellgrau et al., "A Role For CD95 Ligand in Preventing Graft Rejection" Nature, 377:630–632 (Oct. 19, 1995).
Bruce Beutler et al., "Cachectin and Tumour Necrosis Factor As Tow Sides of the Same Biological Coin," Nature, 320:584–588 (Apr. 17, 1986).
Grace Cacalana et al., "Neutrophil and B Cell Expansion in Mice That Lack the Murine IL–8 Receptor Homolog," Science, 265:682–684 (Jul. 29, 1994).

Els Decoster et al., "Generation and Biological Characterization of Membrane–Bound, Uncleavable Murine Tumor Necrosis Factor," J. Biological Chem., 270:30:18473–18478 (1995).
N. Dorrell et al., "Improved Efficiency of Inverse PCR Mutagenesis," BioTechniques 21:604–608 (Oct. 1996).
B.E. Evans et al., "Design of Nonpeptidal Ligands for a Peptide Receptor: Cholecystokinin Antagonists," J. Med. Chem., 30:1229–1239 (1987).
Jean–Luc Fauchére, "Elements for the Rational Design of Peptide Drugs," Advances in Drug Research, 15:29 (1986).
George Georgiou et al., "Display of heterologous proteins on the surface of microorganisms: From the screening of combinatorial libraries to live recombinant vaccines," Nature Biotech, 15:29–34 (1997).
Thomas S. Griffith et al., "Fas Ligand–Induced Apoptosis as a Mechanism of Immune Privelege," Science, 270:1189–1192, Nov. 17, 1995.
M. Hahne et al., "Melanoma Cell Expression of Fas(Apo–1/CD95) Ligand: Implications for Tumor Immune Escape," Science, 274:1363–1366, Nov. 22, 1996.
Michael M. Hann et al., "On the Double Bond Isostere of the Peptide Bond: Preparation of an Enkephalin Analogue," J. Chem. Soc. Perkin Trans. I 307–314 (1982).
Mark W. Holladay et al., "Synthesis of Hydroxyethylene and Ketomethylene Dipeptide Isosteres," Tetrahedron Letters, 24:41:4401–4404 (1983).
Victor J. Hruby, "Conformational Restrictions of Biologically Active Peptides Via Amino Acid Side Chain Groups," Life Sci. 31:189–199 (1982).
Derek Hudson et al., "Methionine Enkephalin and Isosteric Analogues," Int. J. Pept. Prot. Res. 14:177–185 (1979).
Naoto Itoh et al., "The Polypeptide Encoded by the cDNA for Human Cell Surface Antigen Fas Can Mediate Apoptosis," Cell 66:233–243 (1991).
Clive Jennings–White et al., "Synthesis of Ketomethylene Analogs of Dipeptides," Tetrahedron Lett. 23:2533–2534 (1982).
Minoru Kanehisa, "Use of Statistical Criteria for Screening Potential Homologies in Nucleic Acid Sequences," Nuc. Acids Res., 12:1:203–213 (1984).

(List continued on next page.)

Primary Examiner—Lorraine Spector
Assistant Examiner—Eileen B. O'Hara
(74) Attorney, Agent, or Firm—Townsend and Townsend and Crew LLP

(57) ABSTRACT

This invention generally provides polypeptides comprising a noncleavable form of a Fas ligand and having a capacity to activate a Fas receptor-mediated pathway involved in cell death, pharmaceutical compositions of such polypeptides, nucleic acids encoding such polypeptides, and cell lines capable of expressing these nucleic acids. Also provided are therapeutic and prophylactic methods of using such polypeptides, compositions, and cells lines for treating patients suffering from disorders resulting from dysregulation or inappropriate stimulation of the Fas receptor-mediated pathway.

25 Claims, 7 Drawing Sheets

OTHER PUBLICATIONS

Sang–Mo Kang et al., "Fas Ligand Expression In Islets of Langerhans Does Not Confer Immune Privilege and Instead Targets Them for Rapid Destruction," *Nature Medicine*, 3:738–743, Jul. 1997.

Nobuhiko Kayagaki et al., "Metalloproteinase–Mediated Release of Human Fas Ligand," *J. Exp. Med.* 182:1777–1783 (1995).

John F.R. Kerr et al., "Its Significance in Cancer and Cancer Therapy," *Cancer* 73:2013–2026 (1994), published erratum, *Cancer* 73(12):3108 (1994).

Stanley J. Korsmeyer, "Bcl–2 Initiates a New Category of Oncogenes: Regulators of Cell Death," *Blood* 80:879–886 (1992).

M. Kriegler et al., "A Novel Form of TNF/Cechectin Is a Cell Surface Cytotoxic Transmembrane Protein: Ramifications for the Complex Physiology of TNF," *Cell* 53:45–53 (1988).

Henry T. Lau et al., Prevention of Islet Allograft Rejection With Engineered Myoblasts Epxressing FasL in Mice, *Science* 273:109–112 (1996).

J.S. Morley, "Modulation of the Action of Regulatory Peptides by Structural Modification," *Trends Pharm Sci.* 463–468 (1980).

Shigekazu Nagata, "Fas and Fas Ligand: A Death Factor and Its Receptor," *Adv. in Immunol.* 57:129–144 (1994).

Shigekazu Nagata et al., "The Fas Death Factor," *Science* 267:1449–1456 (1995).

Shigekazu Nagata et al., "Fas and Fas Ligand: lpr and gld mutations," *Immunol. Today* 16:39–43 (1995).

Saul B. Needleman et al., "A General Method Applicable to the Search for Similarities in the Amino Acid Sequnce of Two Proteins," *J. Mol. Biol.* 48:443 (1970).

Runzhou Ni et al., "Fas–Mediated Apoptosis in Primary Cultured Mouse Hepatocytes," *Exp. Cell Res.* 215:332–337 (1994).

Alexander Oehm et al., "Purification and Molecular Cloning of the APO–1 Cell Surface Antigen, a Member of the Tumor Necrosis Factor/Nerve Growth Factor Receptor Superfamily," *J. Biological Chem.*, 267:15:10709–10715, May 25, 1992.

Jun Ogasawara et al., "Lethal Effect of the Anti–Fas Antibody in Mice," *Nature* 354:806–809 (1993), published erratum, *Nature* 365:568 (1993).

William R. Pearson et al., "Improved tools for biological sequence comparison," *Proc. Natl. Acad. Sci. (USA)* 85:2444 (1988).

Carl Perez et al., "A Nonsecretable Cell Surface Mutant of Tumor Necrosis Factor (TNF) Kills by Cell–to–Cell Contact," *Cell* 63:251–258 (1990).

Robert M. Pitti et al., "Induction of Apoptosis by Apo–2 Ligand, a New Member of the Tumor Necrosis Factor Cytokine Family," *J. Biological Chem.*, 271:22:12687–12690, May 31, 1996.

Josep Rizo et al., "Constrained Peptides: Models of Bioactive Peptides and Protein Substructures," *Ann. Rev. Biochem.* 61:387 (1992).

Ivan Rodriguez et al., "A bcl–2 Transgene Expressed in Hepatocytes Protects Mice from Fulminant Liver Destruction but Not from Rapid Death Induced by Anti–Fas Antibody Injection," *J. Exp. Med.* 183:1031–1036 (1996).

Temple F. Smith et al., "Comparison of Biosequences," *Adv. Appl. Math.* 2:482 (1981).

A.F. Spatola, Peptide Backbone Modifications, Chemistry and Biochemistry of Amino Acids, Peptides, and Proteins, 7:267–357 (1983) (Boris Weinstein ed. 1983).

A.F. Spatola et al., "Structure–Activity Relationships of Enkephalins Containing Serially Replaced Thiomethylene Amide Bond Surrogates," *Life Sci.*, 38:1243–1249 (1986).

Takashi Suda et al., "Purification and Characterization of the Fas–ligand that Induces Apoptosis," *J. Exp. Med.*, 179:873–879, Mar. 1994.

Tomohiro Takashi et al., "Human Fas ligand: gene structure, chromosomal location and species specificity," *Int'l Immunol.* 6:10 1567–1574 (1994).

Tomohiro Takahashi et al., "Generalized Lymphoproliferative Disease in Mice, Caused by a Point Mutation in the Fas Ligand," Cell 76:969–976 (1994).

De–chu Tang et al., "Genetic immunization is a simple method for eliciting an immune response," *Nature* 356:152–154 (1992).

Masato Tanaka et al., "Fas ligand in human serum," *Nature Med.* 2:3:317–322 (1996).

Masato Tanaka et al., "Expression of the functional soluble form of human Fas ligand in activated lymphocytes," *The EMBO J.* 14:6:1129–1135 (1995).

Pierre Vassali, "The Pathophysiology of Tumor Necrosis Factors," *Ann. Rev. Immunol.* 10:411–452 (1992).

Rie Watanabe–Fukunaga et al., "Lymphoproliferation disorder in mice explained by defects in Fas antigen that mediates apoptosis," *Nature* 356:314–317 (1992).

* cited by examiner

Mutant delta 1:

```
Human TNF-α    pro arg asp leu ser leu ile ser pro leu ala gln --- --- ala|val arg ser
Human FasL     ser gln met his thr ala ser ser|leu glu lys gln ile gly his pro ser pro
                            120                              130
                      70                        90

Human TNF-α    ser ser arg thr pro ser asp lys pro val ala his val val ala asn pro gln
Human FasL     pro pro glu lys glu leu arg lys val ala his leu thr gly lys ser asn
                         140                                       150
                80
```

Mutant delta 2:

```
Human TNF-α    pro arg asp leu ser leu ile ser pro leu ala gln --- --- ala|val arg ser
Human FasL     ser gln met his thr ala ser ser|leu glu lys gln ile gly his pro ser pro
                            120                              130
                      70                        90

Human TNF-α    ser ser arg thr pro ser asp lys pro val ala his val val ala asn pro gln
Human FasL     pro pro glu lys glu leu arg lys val ala his leu thr gly lys ser asn
                         140                                       150
                80
```

Mutant delta 3:

```
Human TNF-α    pro arg asp leu ser leu ile ser pro leu ala gln --- --- ala|val arg ser
Human FasL     ser gln met his thr ala ser ser|leu glu lys gln ile gly his pro ser pro
                            120                              130
                      70                        90

Human TNF-α    ser ser arg thr pro ser asp lys pro val ala his val val ala asn pro gln
Human FasL     pro pro glu lys lys glu leu arg lys val ala his leu thr gly lys ser asn
                         140                                       150
                80
```

FIG. 1.

NONCLEAVABLE FAS LIGAND

STATEMENT OF GOVERNMENT INTEREST

This invention was supported by a grant from the National Institutes of Health (Grant No. PO1-41822) (SB) and the Physician Scientist Award from Howard Hughes Medical Institute (SMK). The Government may have certain rights in this invention.

FIELD OF THE INVENTION

This invention relates generally to the fields of molecular biology and molecular medicine and more specifically to the identification of novel polypeptides comprising a noncleavable form of a Fas ligand and having a capacity to activate a Fas receptor-mediated pathway involved in programmed cell death, and pharmaceutical compositions thereof, and therapeutic and prophylactic methods employing such polypeptides.

BACKGROUND OF THE INVENTION

Programmed cell death, or apoptosis, is a physiological process that guarantees that homeostasis is maintained between cell proliferation and cell differentiation in nearly all self-renewing tissues of multicellular organisms. Apoptosis permits the elimination of cells that are no longer necessary, are produced in excess, have developed improperly, or have sustained genetic damage. A variety of cell types appear to undergo cell death through such an apoptotic mechanism.

In addition to preserving normal tissue homeostasis, apoptosis also occurs in response to a various external stimuli, including cytotoxic lymphokines, radiation, chemotherapeutic agents, growth factor deprivation, hyperthermia, hormone withdrawal, and infection by some viruses. See. e.g., Kerr et al., Cancer 73:2013–2026 (1994), published erratum, Cancer 73(12):3108 (1994). Accordingly, apoptosis is an inducible phenomenon that can be regulated by mechanisms of regulation that are similar to those involved in other metabolic pathways.

Dysregulation of apoptosis has also been observed and is implicated in the development of diseases resulting from inappropriate cell death or inhibition of cell death. For example, apoptotic dysregulation has been observed in some types of cancer cells which survive for longer periods than corresponding normal cells. The inhibition or failure of the apoptotic mechanism may permit such cells to undergo mutations leading to a transformed or cancerous state. See. e.g., Korsmeyer, Blood 80:879–886 (1992). Inhibition or failure of the apoptotic cell death mechanism may also contribute to diseases of the immune system by allowing persistence of self-reactive B and T lymphocyte cells, thereby promoting autoimmune disorders. See. e.g., Watanabe-Fukunaga et al., Nature 356:314–317 (1992). Apoptotic dysregulation has also been observed in neurodegenerative diseases in which neurons die prematurely.

Apoptosis is mediated, at least in part, by a cell surface receptor protein known as the Fas antigen receptor ("Fas") (also known as "APO-1 antigen" or "CD95"). Fas is an approximately 45-kDa (kiloDalton) type I transmembrane protein belonging to the tumor necrosis factor ("TNF")/nerve growth factor ("NGF") receptor family of proteins. Tanaka et al., Nature Med. 2:317–322 (1996); Tanaka et al., EMBO J. 14:1129–1135 (1995). Fas is expressed in a variety of tissues, including the thymus, liver, lung, intestine, heart, and kidney, and in various human cell types, including, for example, lymphocytes, hepatocytes, activated B and T cells, and neutrophils, and carcinoma cells, such as breast, colon, prostate and pancreatic cancer cells. Tanaka et al., Nature Med. 2:317–322 (1996); Kayagaki et al., J. Exp. Med. 182:1777–1783 (1995). As a receptor protein, Fas has been found to transduce extracellular signals into a cell and, as a result, can mediate or trigger apoptosis. Itoh et al., Cell 66:233–243 (1991).

Because Fas is expressed on the cell surface, its mechanism of action is believed to be regulated by interacting with or binding to another cell surface protein. One such known protein is Fas ligand ("FasL"), a 40-kDa type II transmembrane protein of the TNF family. FasL has been observed to mediate and induce apoptosis by binding to Fas. Takahashi et al., Int'l Immunol. 6:1567–1574 (1994); Abbas, Cell 84:655–657 (1996). Human FasL is a polypeptide of 281 amino acids divided into three distinct domains—an intracellular (i.e., cytoplasmic) domain, a transmembrane domain, and an extracellular domain. See, e.g., EP Patent Application, Publ. No. 0 675 200 A1 (published Oct. 4, 1995, issued to Mochida Pharmaceutical Co., Ltd.). FasL is predominantly expressed in activated T cells, but is also expressed in a number of other cell types, including Sertoli cells in the testis and the stroma cells of the retina. Tanaka et al., Nature Med. 2:317–322 (1996).

The interaction between FasL and Fas has been shown to be critical to the regulation of cell number in a large number of tissue and organ systems. Nagata, Adv. in Immunol. 57:129–144 (1994); Nagata et al., Science 267:1449–1456 (1995). The Fas/FasL system has been implicated, for example, in the pathogenesis of fulminant hepatitis, GVHHD, and AIDS. Kayagaki et al., J. Exp. Med. 182:1777–1783 (1995). Loss of function of the Fas/FasL system has also been observed to result in lymphoproliferative disorders and to accelerate autoimmune disorders in humans and mice. Takahashi et al., Cell 76:969–976 (1994).

Conversely, exaggeration of the Fas system appears to cause tissue damage. Tanaka et al., Nature Med. 2:317–322 (1996). Fas expression is upregulated in hepatocytes transformed by human hepatitis C virus. Lymphocytes transformed with human immune deficiency virus ("HIV"), human T cell leukemia ("HTLV-1") or Epstein-Barr virus ("EBV") express a high level of Fas and appear to be sensitive to Fasmediated apoptosis. Tanaka et al., Nature Med. 2:317–322 (1996).

The Fas/FasL interaction has been particularly well studied in the immune system. The activation of T cells through the T cell receptor ("TCR") upregulates both Fas and FasL on such cells. In circumstances of low to moderate TCR stimulation, T cells proliferate. Under conditions of repetitive or high levels of TCR stimulation, T cells are driven toward apoptosis. This phenomenon has been termed "Antigen Induced Cell Death" ("AICD"). The importance of AICD in regulating the immune system has been demonstrated in the LPR mouse. Nagata et al., Immunol. Today 16:39–43 (1995). This mouse strain, which has a spontaneous disruption in the Fas gene from the insertion of an endogenous retroviral element, has been shown to be defective in AICD. With age, such mice develop large numbers of non-functional T lymphocytes in lymphoid and non-lymphoid tissues and develop a number of autoimmune syndromes.

The Fas/FasL system also appears to contribute to the phenomenon of immune privilege. It has been shown that in the testis and the anterior chamber of the eye, constitutive expression of FasL may serve to limit the immune response by eliminating Fas-bearing T cells and possibly other Fas-bearing inflammatory cell types. Bellgrau et al., *Nature* 377:630–632 (1995); Griffith et al., *Science* 270:1189–1192 (1995). The Fas system appears to maintain the immune privilege by preventing activated lymphocytes from infiltrating the testis or testis. In the case of the testis, it has been shown that FasL-bearing Sertoli cells can be transplanted across major histocompatibility complex ("MHC") barriers, with constitutive FasL expression protecting against alloimmune mechanisms. Bellgrau et al., supra. This demonstration has inspired a number of investigators to study the possibility of artificially conferring immune privilege to transplanted organs via the induction of FasL expression. It has also been shown that syngeneic myoblasts expressing FasL can protect allogenic islets from alloimmune destruction. Lau et al., *Science* 273:109–112 (1996).

The mechanism of action by which FasL interacts with Fas and mediates apoptosis has been examined rather extensively. Recent studies have shown that membrane-bound FasL is converted to a soluble 26-kDa form of FasL ("sFasL") by action of a matrix metalloproteinase-like enzyme. Kayagaki et al., *J. Exp. Med.* 182:1777–1783 (1995); Tanaka et al., *Nature Med.* 2:317–322 (1996); Tanaka et al., *EMBO J.* 14:1129–1135 (1995). Soluble human FasL is believed to comprise an amino acid sequence of the extracellular domain of FasL which has been proteolytically cleaved from membrane-bound FasL and released into the surrounding body fluid or cell culture supernatant. See. e.g., EP Patent Application, Publ. No. 0 675 200 A1, supra. Soluble FasL is an active form of FasL; it has been shown to bind to Fas antigen receptor and thus to induce apoptosis. Tanaka et al., *Nature Med.* 2:317–322 (1996).

That apoptosis is mediated by a soluble form of FasL is not surprising given that FasL is homologous with TNF. It is well known that a secretory (soluble) form of TNF is released from the membrane-bound form of TNF by metalloprotease action at the cell surface of activated macrophages and T cells. Kriegler et al., *Cell* 53:45–53 (1988). Soluble TNF has been detected in the serum of patients with malignant tumor cells or with septic shock. Beutler and Cerami, *Nature* 320:584–588 (1986); Vassalli, *Ann. Rev. Immunol.* 10:411–452 (1992). Soluble TNF has been shown to be a biologically active form of TNF which can kill target cells bearing its receptor. Widespread release of soluble TNF into the circulatory system of an individual has been observed to precipitate systemic tissue damage. See. e.g., Perez et al., *Cell* 63:251–258 (1990). TNF is believed to kill its targets by either cell-to-cell contact through the transmembrane form of TNF or by local release of the TNF secretory component into the circulatory system of an individual. Id.

The proteolytic cleavage of FasL from the cell membrane to which it is bound appears to be quite efficient because inhibitors of matrix metalloproteases have been found to increase greatly the expression of membrane-bound FasL. These results suggest that the majority of translated FasL is cleaved. Indeed, FasL cannot be detected on some cell types by fluorescence activated cell sorting without also employing metalloprotease inhibitors. Kayagaki et al., *J. Exp. Med.* 182:1777–1783 (1995).

Because soluble FasL is released into and circulates widely throughout the circulatory system, it has the ability to bind to Fas-expressing cells throughout the body, resulting in nonspecific and widespread cell death. The potential toxicity of systemic Fas activation has been shown by the administration of agonistic anti-Fas antibody to mice. Such mice died within hours of antibody administration due to rapid liver failure resulting from fulminant hepatocyte death. Ogasawara et al., *Nature* 364:806–809 (1993), published erratum, *Nature* 365:568 (1993). Measurable levels of soluble FasL have also been reported in a number of human disease states and soluble FasL has been implicated as the causative agent for the idiopathic hepatitis and bone marrow suppression which is often seen in patients suffering from such disorders. Tanaka et al., *Nature Med.* 2:317–322 (1996). The potential toxicity of soluble FasL is also expected on numerous other tissues that express Fas, since soluble FasL is released from the cell membrane and can be transported all over the body. Mice expressing bcl-2 in hepatocytes, for example, have been shown to be protected from anti-Fas antibody mediated hepatocyte death. However, such mice were not found to be protected from death. Rodriguez et al., *J. Exp. Med.* 183:1031–1036 (1996).

It would be desirable to be able to modulate the expression of FasL and the interaction of FasL with Fas so as to be able to selectively modulate and induce apoptosis of specific targets, including particular tissues, organs, and cells. It would be especially desirable to be able to regulate the production of soluble FasL so as to prevent and/or minimize the deleterious effects of soluble FasL in the body, including the widespread and nonspecific cell, organ, and tissue death resulting from the circulation of soluble FasL throughout the body and its indiscriminate and damaging effects on a wide variety of cells, tissues, and organs. Such regulation would allow for the treatment and/or prevention of various symptoms resulting from diseases and disorders characterized by inadequate stimulation of the Fas receptor-mediated pathway or by inappropriate action or stimulation by soluble FasL on Fas receptors on cells, tissues, and organs throughout the patient's body. As noted above, such regulation is made difficult by the fact that membrane-bound FasL is cleaved proteolytically to form soluble FasL which is released into local or systemic circulation, thereby causing nonspecific tissue and cell damage locally and systemically. Such regulation would also allow for the treatment and/or prevention of various symptoms resulting from diseases and disorders characterized by inadequate or inappropriate stimulation of the Fas receptor-mediated pathway. Thus, a need exists for a noncleavable form of FasL which can be used in artificially and selectively modulating apoptosis in various cells, tissues, and organs, and for reagents, compositions, and methods employing such noncleavable forms of FasL for use in therapeutic and prophylactic treatment of disorders responsive to the Fas-mediated pathway. This invention meets these and other needs.

SUMMARY OF THE INVENTION

In one embodiment of the invention, polypeptides having a capacity to activate a Fas receptor-mediated pathway are provided. Many of these polypeptides comprise amino acid sequences having at least 80% sequence identity with the amino acid sequence of SEQ ID NO:1, but differing from SEQ ID NO:1 by at least one mutation within a Fas ligand (FasL) protease recognition region which comprises an amino acid sequence within SEQ ID NO:1. The FasL protease recognition region comprises an amino acid sequence within SEQ ID No:1. The mutation inhibits proteolytic cleavage of the polypeptide from a first cell membrane to which the polypeptide is bound relative to proteolytic cleavage of SEQ ID NO:1 from a second cell membrane to which SEQ ID NO:1 is bound. Many such polypeptides bind to the Fas receptor, and in many instances, the Fas receptor-mediated pathway is apoptosis. Some such polypeptides comprise a full-length Pas ligand, while some polypeptides comprise an allelic or species variant of SEQ ID NO:1.

In many such polypeptides, the mutation comprises deletion of at least one amino acid residue from an amino acid sequence of the FasL protease recognition region, substitution of at least one amino acid residue in an amino acid sequence of the FasL protease recognition region, insertion of at least one additional amino acid residue into an amino acid sequence of the FasL protease recognition region, or any combination thereof. In some polypeptides, the mutation comprises deletion of at least one amino acid residue between residue 118 and residue 155 of SEQ ID NO:1 or an allelic or species variation thereof.

In another aspect of the invention, polypeptides comprising a modified FasL protease recognition region and having a capacity to activate a Fas receptor-mediated pathway are provided. The proteolytic cleavage of these polypeptides from a first cell membrane to which the polypeptide is bound is reduced relative to the proteolytic cleavage of wild-type FasL from a second cell membrane to which the wild-type FasL is bound. Usually, the modified FasL protease recognition region of such polypeptides is formed by a wild-type FasL protease recognition region having at least one amino acid mutation, and the Fas receptor-mediated pathway is apoptosis.

In another aspect, the invention provides polypeptides having at least 80% sequence identity with the amino acid sequence of SEQ ID NO:1 and a capacity to activate a Fas receptor-mediated pathway. Such amino acid sequence differs from the sequence of SEQ ID NO:1 by at least one mutation within a FasL protease recognition region within SEQ ID NO:1. The FasL protease recognition region comprises an amino acid sequence within SEQ ID NO:1. The mutation inhibits proteolytic cleavage of the polypeptide from a cell membrane to which it is bound relative to proteolytic cleavage of SEQ ID NO:1 from a cell membrane to which SEQ ID NO:1 is bound.

In another aspect of the invention, polypeptides comprising an extracellular domain of a FasL are provided. The extracellular domain has a capacity to activate a Fas receptor-mediated pathway. Furthermore, such polypeptides are linked to a cell membrane by a linker between the extracellular domain and the cell membrane, such that on cleavage of FasL with a protease, such as a metalloprotease, the domain remains linked to the cell membrane.

In yet another aspect of the invention, fusion proteins having at least two components are provided. The first component comprises a polypeptide comprising an amino acid sequence having at least 70%, 80%, 85%, or 90% sequence identity with the amino acid sequence of SEQ ID NO:1, said sequence differing from SEQ ID NO:1 by at least one mutation within a FasL protease recognition region within SEQ ID NO:1, whereby the mutation inhibits proteolytic cleavage of the polypeptide from a first cell membrane to which the polypeptide is bound relative to proteolytic cleavage of SEQ ID NO:1 from a second cell membrane to which SEQ ID NO:1 is bound. The second component comprises a heterologous protein linked to a membrane of a cell.

In another aspect of the invention, pharmaceutical compositions comprising a polypeptide of the invention, as described above, in a pharmaceutically acceptable carrier are provided.

The invention also provides compositions comprising a vector containing a nucleic acid sequence encoding a polypeptide of the invention, as described above, and a pharmaceutically acceptable carrier. Some such compositions further comprise lipids complexed with the vector.

In addition, the invention provides nucleic acid sequences encoding a polypeptide of the invention, as described above.

In another aspect, the invention provides isolated host cells containing a nucleic acid sequence encoding a polypeptide of the invention. Some host cells are mammalian cells. Furthermore, for some such host cells, the polypeptide resides on the surface of the cell. Compositions comprising such cells are also provided.

Also provided by the invention are pharmaceutical compositions comprising a pharmaceutically acceptable carrier and an isolated host cell containing a nucleic acid sequence encoding a polypeptide of the invention, as described above.

In another aspect, the invention provides vectors containing a nucleic acid sequence encoding a polypeptide of the invention, as described above.

In yet another aspect of the invention, methods of alleviating a symptom of a patient suffering from a disorder that is characterized by inadequate or inappropriate stimulation of a Fas receptor-mediated pathway in a tissue or an organ of the patient are provided. Such methods comprise delivering to the tissue or organ of the patient an effective amount of a cell containing a nucleic acid sequence encoding a polypeptide of the invention, as described above.

The invention also provides methods of alleviating a symptom of a patient suffering from a disorder that is characterized by inadequate or inappropriate stimulation of a Fas receptor-mediated pathway in a cell, a tissue, or an organ of the patient. Such methods comprise delivering to the cell, tissue, or organ of the patient an effective amount of a polypeptide of the invention that is linked to a pharmaceutically acceptable carrier having an affinity for the cell, tissue, or organ.

In another aspect of the invention, methods of modifying the phenotype of cells are provided. Such methods comprise contacting the cells with a pharmaceutical composition such that the phenotype of the cells is modified. The pharmaceutical composition comprises a vector containing a nucleic acid sequence encoding a polypeptide of the invention, as described above, and a pharmaceutically acceptable carrier. Usually, in such methods, the nucleic acid sequence integrates into the genome of the cells and is expressed, or replicates autonomously of the genome of the cells and is expressed. For some such methods, the cells are from a tissue or an organ of a patient suffering from a disorder characterized by inadequate or inappropriate stimulation or action of a Fas receptor-mediated pathway, and the method further comprises delivering such cells to the tissue or organ of the patient after modifying the phenotype of the cells.

The invention also provides isolated organs or tissues on which a polypeptide of the invention resides. Such polypeptide results from expression of a nucleic acid sequence encoding the polypeptide. The nucleic acid sequence is integrated into the genome of cells of the organ or tissue, or replicates autonomously of the genome of the cells, and is expressed.

Also provided are methods of alleviating a symptom of a patient suffering from a disorder that is characterized by inadequate or inappropriate stimulation or action of a Fas receptor-mediated pathway which comprise introducing into the patient an organ or tissue of the invention, as described above.

In another aspect of the invention, methods for the prophylactic or therapeutic treatment of intolerance to a graft in a patient are provided. Such methods comprise delivering to the graft of the patient an effective amount of a polypeptide of the invention.

Also included are methods for the prophylactic or therapeutic treatment of intolerance to a graft in a patient which comprise delivering to the graft of the patient an effective amount of a polypeptide of the invention that is linked to a pharmaceutically acceptable carrier. In some such methods, the carrier has an affinity for the graft.

Additionally, the invention provides methods of protecting an organ or tissue from autoimmune destruction in a patient in need of such treatment. Such methods comprise delivering to the organ or tissue of the patient an effective amount of a polypeptide of the invention. In such methods, the polypeptide has an affinity for the organ or tissue.

Also provided are methods for the prophylactic or therapeutic treatment of intolerance to a graft in a patient in need of such treatment. Such methods comprise delivering to the patient a graft on which a polypeptide of the invention, as described above, resides. Such polypeptide results from expression of a nucleic acid sequence encoding the polypeptide. The nucleic acid sequence is integrated into the genome of cells of the graft, or replicates autonomously of the genome of the cells, and is expressed.

BRIEF DESCRIPTION OF THE DRAWINGS

FIG. 1 shows the amino acid sequences of the metalloprotease recognition regions for human TNF-α and human FasL, respectively. The known cleavage site of human TNFα is indicated by a vertical line between amino acid residue 76 (alanine) and amino acid residue 77 (valine). Perez et al., *Cell* 63:251–258 (1990). The twelve contiguous (12) amino acid residues that were deleted from human wild-type TNF-α by Perez et al. in preparing a noncleavable, functional mutant form of TNFα are shown in bold type (i.e., amino acid residues 77 to 88). Id. Also shown in bold type are the amino acid sequences that were deleted from human wild-type FasL in preparing three mutant forms of human FasL for the present invention. The postulated proteolytic cleavage site of human FasL is indicated by a vertical line between amino acid residue 126 (serine) and amino acid residue 127 (leucine) of FasL. Deletion mutant 1 ("mutant delta 1") (SEQ ID NO:3) was prepared by deleting, via site-directed mutagenesis, the codons encoding amino acid residues 126 to 129 of wild-type human FasL. Deletion mutant 2 ("mutant delta 2") (SEQ ID NO:4) was prepared by deleting, via site-directed mutagenesis, the codons encoding amino acid residues 126 to 135 (inclusive) of wild-type human FasL. Deletion mutant 3 ("mutant delta 3") (SEQ ID NO:5) was create by deleting, via-site-directed mutagenesis, the codons encoding amino acid residues 126 to 145 of wild-type human FasL. All residues are numbered by reference to the known amino acid sequence of wild-type human FasL. See Takahashi et al., *Int'l Immunol.* 6:1567–1574 (1994).

DETAILED DESCRIPTION OF THE PREFERRED EMBODIMENT

I. Definitions

Figure 2:
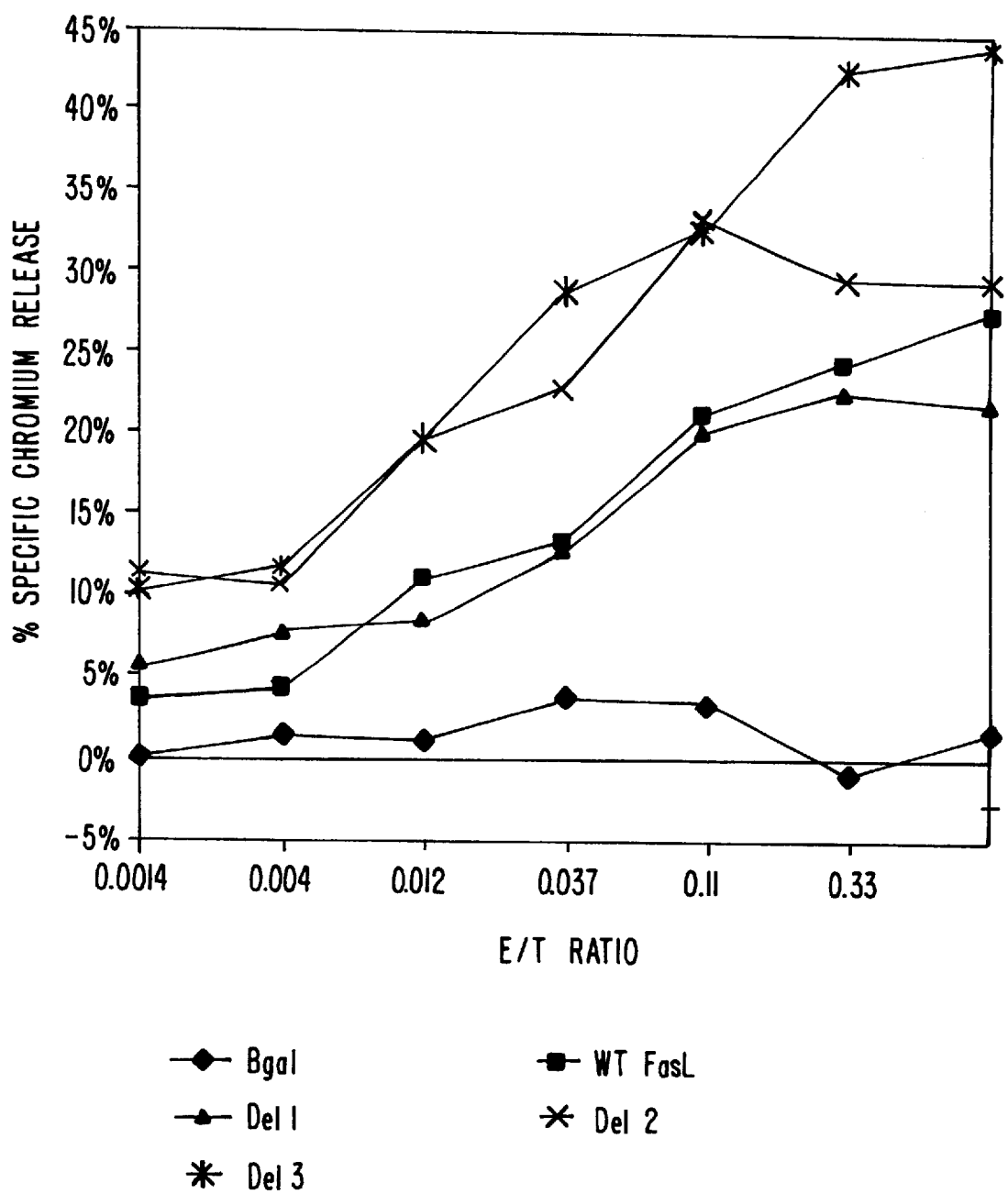
FIG. 2 shows a cytotoxicity assay for COS-7 cells transfected with a wild-type human Fas ligand construct ("WT FasL") (—■—), deletion mutant 1 ("Del 1") (—▲—), deletion mutant 2 ("Del 2") (—X—), or deletion mutant 3 ("Del 3") (—✕—) ("effector cells"), as described in the Examples below. Jurkat T cells loaded with chromium-51 [$^{51}$Cr] were used as target cells. COS-7 cells transfected with a CMV β-galactosidase construct ("Bgal") (—♦—) were used as a negative control. Results are expressed as the percent of specific $^{51}$Cr released, which equals 100 times $^{51}$Cr cpm (counts per minute) released from cells incubated with effector cells minus $^{51}$Cr cpm released in the presence of medium alone divided by $^{51}$Cr cpm released in detergent (maximum release) minus $^{51}$Cr cpm released in medium alone, versus the ratio of effector cells to target cells (the "E/T ratio"). Cell death and the degree of apoptosis induced by the various mutant constructs are reflected by the percentage of $^{51}$Cr released from the Jurkat cells due to induced apoptosis and lysis of such cells.
Figure 3C:
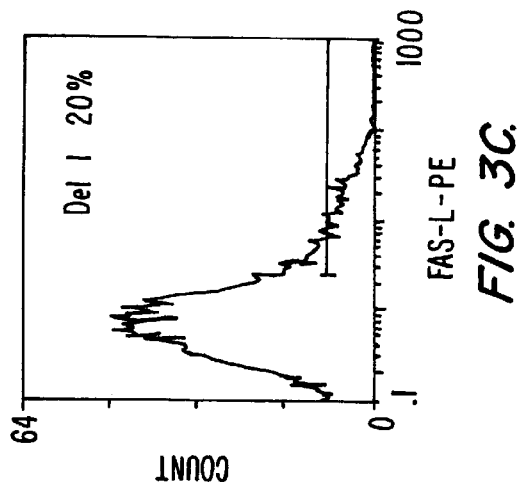
FIG. 3 shows a fluorescence-activated cell sorting ("FACS") analysis of FasL expression on COS-7 cells transfected with wild-type human FasL ("WT") or with deletion mutant 1 ("Del 1"), deletion mutant 2 ("Del 2"), or deletion mutant 3 ("Del 3"), as described in the Examples below. COS-7 cells transfected with a CMV β-galactosidase construct ("Bgal") were used as a negative control. Forty-eight hours after transfection, COS-7 cells were lightly trypsinized and stained with a biotinylated monoclonal antibody to human FasL (i.e., NOK-1). Bound antibody was detected using phycoerythrin (PE)-conjugated streptavidin. The labelled bound antibody/human FasL construct complex is designated as Fas-L-PE. Results are expressed as relative cell number ("Count") versus log of the fluorescence intensity of the labelled bound antibody/human FasL construct ("Fas-L-PE"). Approximately twice as many cells stained positively for FasL when transfected with deletion mutants 2 and 3 ("Del 2"and "Del 3," respectively).
Figure 3B:
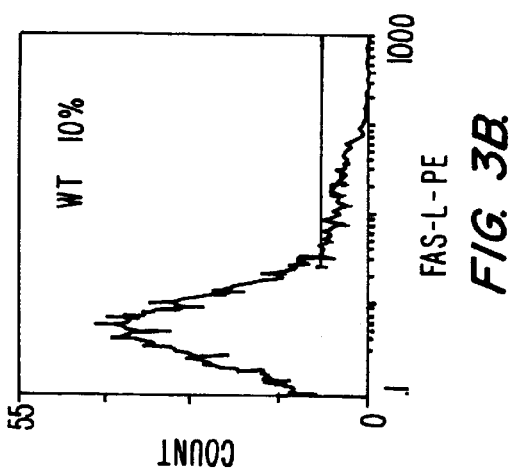
Figure 3E:
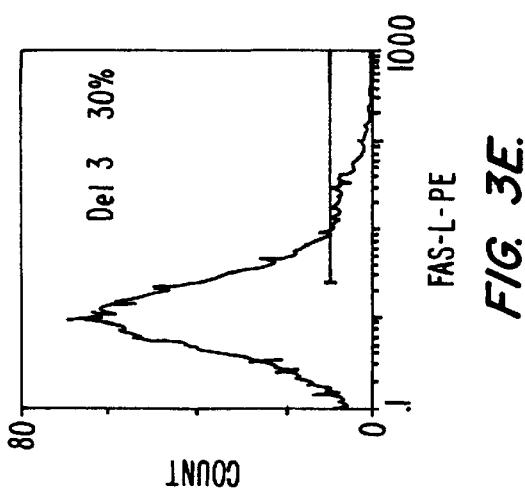
Figure 3A:
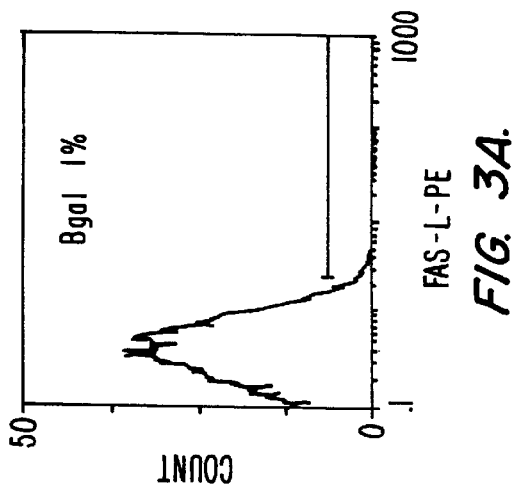
Figure 3D:
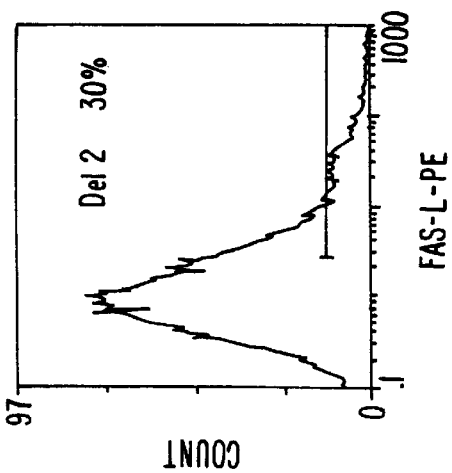

The term "naturally occurring" as applied to an object refers to the fact that an object can be found in nature. For example, a polypeptide or polynucleotide sequence which is present in an organism (including viruses) that can be isolated from a source in nature and which has not been intentionally modified by man in the laboratory is naturally occurring. A nucleotide sequence of "naturally occurring" FasL means a nucleotide sequence of wild-type FasL, such as is shown in SEQ ID NO:2, or an allelic or species variation thereof or biologically active fragment thereof. An amino acid sequence of "naturally occurring" FasL means an amino acid sequence of wild-type FasL, such as is shown in SEQ ID NO:1, or an allelic or species variation thereof or biologically active fragment thereof.

The term "Fas ligand protease recognition region" or "FasL protease recognition region" refers to a sequence of amino acids of wild-type FasL that is recognized by a site-specific protease, including a metalloprotease, similar enzyme, or the like, that in nature cleaves a FasL from a cell membrane (to which FasL is bound or attached). The term includes a full-length FasL protease recognition region and biologically active fragments thereof, including those discussed below, and combinations thereof. The FasL protease recognition region is found in humans and non-human mammals, including mice. The protease recognition region of wild-type, full-length human FasL, which is shown in SEQ ID NO:1, comprises at least an amino acid sequence within the extracellular domain of wild-type, full-length human FasL. The extracellular domain of wild-type human FasL comprises amino acid residues 103 to 281 of SEQ ID NO:1. In one embodiment of the present invention, the protease recognition region of wild-type human FasL comprises at least amino acid residue 119 to amino acid residue 154 of SEQ ID NO:1.

The term "modified FasL protease recognition region" (or "modified nonnaturally occurring FasL protease recognition region") refers to a protease recognition region of wild-type FasL that has been altered, modified, or changed such that proteolytic cleavage by a site-specific protease from the cell membrane to which the subject FasL is bound of all, substantially all, or a portion of the extracellular domain of the FasL is reduced or inhibited relative to proteolytic cleavage of all, substantially all or a portion of the extracellular domain of wild-type FasL from the cell membrane to which wild-type FasL is bound. A. modified FasL protease recognition region can be produced by various means, including, e.g., by at least one amino acid mutation within the protease recognition region of the extracellular domain of FasL. Such mutation may occur naturally or may be generated artificially in the laboratory. Alternatively, a modified FasL protease recognition region can be cause by intentional alteration, modification, or change of wild-type FasL in the laboratory, such as, e.g., by linking the wild-type FasL extracellular domain to a cell membrane via (e.g., a covalent linkage or other linkage that is not affected by action of a site-specific protease, such as a metalloprotease) so that the action of the protease cannot serve to separate the domain completely from the cell membrane (i.e., the extracellular domain remains linked, coupled to, or bound to the cell membrane). In one embodiment of the invention, proteolytic cleavage of the modified FasL is reduced or inhibited such that 0% or less than 5%, 10%, 20%, 30%, 40%, 50%, 60%, or 70% of soluble FasL is released from the cell membrane to which the modified FasL is bound relative to proteolytic cleavage of wild-type FasL from the cell membrane to which modified FasL by the site-specific protease.

The term "epitope" includes any protein determinant capable of specific binding to an immunoglobulin or T-cell receptor. Epitopic determinants usually consist of chemically active surface groupings of molecules such as amino acids or sugar side chains.

The term "linker" refers to a means for connecting, coupling, anchoring or attaching one component or entity to another component or entity. The term "linked" refers to the connecting, coupling, anchoring or attaching of one component or entity to another component or entity.

A "noncleavable form of FasL" or "noncleavable FasL" means a polypeptide having a modified FasL protease recognition region within the extracellular domain of FasL such that proteolytic cleavage by a site-specific protease (e.g., metalloprotease) of all, substantially all, or a portion of the FasL from a cell membrane to which it is bound is reduced or inhibited relative to proteolytic cleavage of wild-type FasL from a cell membrane to which wild-type FasL is bound. In contrast with wild-type FasL, which is at least substantially converted to a soluble form of FasL by proteolytic action, with noncleavable FasL, little, substantially none, or none of noncleavable FasL is converted to soluble FasL by the site-specific protease. In one embodiment of the invention, proteolytic cleavage of noncleavable FasL is reduced or inhibited such that 0% or less than 5%, 10%, 20%, 30%, 40%, 50%, 60%, or 70% of soluble FasL is released by action of the site-specific protease from the cell membrane to which noncleavable FasL is bound relative to proteolytic cleavage by the protease of wild-type FasL from the cell membrane to which wild-type FasL is bound.

The term "substantially all or a portion" in reference to proteolytic cleavage of a polypeptide from a cell membrane to which it is bound or linked (e.g., cleavage of wild-type FasL or a polypeptide of the invention) means that usually at least about 30%, 40%, 50%, 60%, 70%, 80%, 90%, 95%, or 99% of such polypeptide is cleaved from the cell membrane by action of a site-specific protease (e.g. metalloprotease).

The term "biologically active fragment" as pertains to polypeptides means polypeptides possessing one of the particular biological activities described herein. Polypeptides or biologically active fragments thereof include, for example, polypeptides that activate, initiate, or stimulate Fas receptor-mediated pathways (such as apoptosis) by binding to or interacting with a Fas antigen receptor, induce apoptosis, or affect the interaction of the Fas receptor with wild-type FasL (e.g., by blocking or otherwise inhibiting binding of the wild-type FasL to the Fas receptor).

Also included within the definition of "biologically active fragments" are those polypeptides or fragments of the invention which are characterized by their ability to bind antibodies raised against proteins or polypeptides having the amino acid sequence of SEQ ID NO:1 (or allelic or species variation thereof) or biologically active fragments thereof. Such antibodies generally recognize polypeptides that are substantially homologous to the polypeptide shown in SEQ ID NO:1 (or allelic or species variations thereof) or biologically active fragments thereof. A variety of immunoassay formats are used to select antibodies specifically immunoreactive with a particular protein or polypeptide domain. For example, solid-phase ELISA immunoassays are routinely used to select monoclonal antibodies specifically immunoreactive with a protein. See Harlow and Lane *ANTIBODIES, A LABORATORY MANUAL* (Cold Spring Harbor Publ., New York 1988) for a description of immunoassay formats and conditions that can be used to determine specific immunoreactivity.

The term "patient" includes animals, humans and other mammals, including mice.

The term "host cell" generally refers to isolated or cultured prokaryotic or eukaryotic organisms and includes any transformable organism which is capable of expressing a protein and can be, or has been, used as a recipient for expression vectors or other transfer DNA. Host cells containing nucleic acids of the invention and for expression vectors comprising such nucleic acids include mammalian cells, such as endocrine cells, COS cells, neuronal cells, embryonic stem cells, dendritic cells or other antigen-presenting cells, lymphocytes or other cells of lymphoid origin, hemopoietic stem cells or cells of hemopoietic origin, and neuronal cells.

The following terms are used to describe the sequence relationships between two or more polypeptides: "reference sequence", "sequence identity", "percentage of sequence identity", and "substantial identity". As applied to polypeptides, the term "substantial identity" means that two peptide sequences, when optimally aligned, such as by the programs GAP or BESTFIT using default gap weights, share at least 60 percent sequence identity, typically at least 70 percent sequence identity, usually at least 80 percent sequence identity, preferably at least 85 percent sequence identity, more preferably at least 90 percent sequence identity, and even more preferably at least 95 percent sequence identity or more (e.g., 99 percent sequence identity). Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. Percentage sequence identities are determined by the programs GAP and BESTFIT using default gap weights.

The term "allelic variation" in the context of a nucleic acid or a gene means an alternative form (allele) of a gene that exists in more than one form in the population. At the polypeptide level, "allelic variants" generally differ from one another by only one or, at most, a few amino acid substitutions. A "species variation" of a nucleic acid or a polypeptide is one in which the variation is wild type among different species of an organism. A "cognate variation" of a nucleic acid or a polypeptide is one in which the variation is evolutionarily and functionally related between species. For example, in the human genome, the human CD4 gene is the cognate gene to the mouse CD4 gene, since the sequences and structures of these two genes indicate that they are highly homologous and both genes encode a protein which functions in signaling T-cell activation through MHC class II-restricted antigen recognition.

The term "recombinant" or "recombinant DNA molecule" refers to a nucleic acid sequence which is not a naturally occurring or wild-type sequence, or is made by the artificial combination of two otherwise separated segments of sequence. By "recombinantly produced" is meant artificial combination often accomplished by either chemical synthesis means, or by the artificial manipulation of isolated segments of nucleic acids, such as, for example, by genetic engineering techniques. Such can be done to replace a codon with a redundant codon encoding the same or a conservative amino acid, while typically introducing or removing a sequence recognition site. Alternatively, it is performed to join together nucleic acid segments of desired functions to generate a single genetic entity comprising a desired combination of functions not found in the common natural forms. Restriction enzyme recognition sites are often the target of such artificial manipulations, but other site specific targets (e.g., promoters, DNA replication sites, regulation sequences, control sequences), or other useful features may be incorporated by design. "Recombinant DNA molecules" include cloning and expression vectors.

The technique of "polymerase chain reaction" (or "PCR") generally refers to a procedure wherein minute amounts of a specific piece of nucleic acid, RNA and/or DNA, are amplified as described in U.S. Pat. No. 4,683,195. Generally, sequence information from the ends of the region of interest or beyond needs to be available, such that oligonucleotide primers can be designed. These primers will be identical or similar in sequence to opposite strands on the template to be amplified. The 5' terminal nucleotides of the two primers coincide with the ends of the amplified material. PCR can be used to amplify specific RNA sequences, specific DNA sequences from total genomic DNA, and cDNA transcribed from total cellular RNA, bacteriophage or plasmid sequences, etc. See generally, Mullis et al., *Cold Spring Harbor Symp. Quant. Biol.* 51:263 (1987); PCR TECHNOLOGY (Erlich ed., 1989). PCR is one, but not the only, example of a nucleic acid polymerase reaction method for amplifying a nucleic acid test sample, comprising the use of a known nucleic acid (DNA or RNA) as a primer.

A "primer" or "oligonucleotide" can be a single-stranded polynucleotide that may be chemically synthesized by known methods. Suitable oligonucleotides are prepared by the phosphoramidite method described by Beaucage and Carruthers, *Tetr. Lett.* 22:1859 (1981), by the triester method according to Matteucci et al., *J. Am. Chem. Soc.* 103:3185 (1981), or by other methods, such as by using commercial automated oligonucleotide synthesizers (e.g., Applied Bio Systems oligonucleotide synthesizer) according to the specifications provided by the manufacturer.

II. Polypeptides of the Invention

The invention generally provides polypeptides that have a capacity to activate or stimulate and/or do activate or stimulate Fas-mediated pathways via interaction with, association with, or binding to Fas. Such polypeptides typically comprise a modified FasL protease recognition region and have a capacity to activate a Fas receptor-mediated pathway, wherein proteolytic cleavage by a site-specific protease (e.g., metalloprotease or similar enzyme) of all, substantially all or a portion of the polypeptide from a membrane to which the polypeptide is bound is reduced relative to such proteolytic cleavage of all, substantially all or a portion of wild-type FasL from a cell membrane to which wild-type FasL is bound.

Naturally occurring (or wild-type) full length human FasL is a type II transmembrane TNF-related protein of 281 amino acid residues comprising three amino acid sequence domains: an intracellular domain, a transmembrane domain, and an extracellular domain. The extracellular domain (also termed "extracellular region") is located on the external surface of the cell membrane to which FasL is bound. In human FasL, the extracellular domain comprises the amino acid sequence of from the 103rd amino acid residue to the 281st amino acid residue of full-length FasL. It is believed that this extracellular domain includes a sequence of amino acids that is recognized by a protease (e.g., a matrix metalloprotease or similar enzyme). Such sequence is termed a "protease recognition region" (or "protease recognition site") as described above. Through a recognition mechanism, the protease cleaves and separates all, substantially all or a portion of the extracellular domain of FasL from the remainder of FasL and from the surface of the cell membrane to which FasL is bound. Kayagaki et al., *J. Exp. Med.* 182:1777–1783 (1995); Tanaka et al., *Nature Med.* 2:317–322 (1996). The protease recognition region of human FasL comprises at least amino acid residue 119 to amino acid residue 154 of wild-type, full-length human FasL, as shown in SEQ ID NO:1.

The particular site in the amino acid sequence of the extracellular domain at which FasL is cleaved and separated from the cell membrane is termed the "cleavage site." The FasL cleavage site is not limited to any particular site and may change depending on the conditions of the cell culture or proteases present inside or outside the cell. It is likely that all, substantially all or a portion of the extracellular domain of FasL is released by proteolytic action from the cell membrane into the supernatant of a cell culture or into body fluids, such as urine and blood. As noted above, the released subunit of full-length FasL is termed "soluble FasL" and comprises a soluble 26-kDa glycoprotein. Tanaka et al., *EMBO J*. 14:1129–1135 (1995). Soluble FasL appears to be an active form of FasL that binds to Fas expressed on the surface of certain cells, thereby activating apoptotic signal transduction. Tanaka et al., *Nature Med.* 2:317–322 (1996).

In contrast with the wild-type protease recognition region of wild-type FasL, a polypeptide of the invention comprises a modified FasL protease recognition region such that proteolytic cleavage of all, substantially all or a portion of the extracellular domain of the polypeptide from a cell membrane to which it is bound or linked is reduced or inhibited relative to proteolytic cleavage of all, substantially all or a portion of the extracellular domain of wild-type FasL from a cell membrane to which wild-type FasL). Polypeptides of the invention typically comprise an extracellular domain of amino acids that resides on the surface of a cell. Polypeptides of the invention also include an amino acid sequence incorporated into or spanning the membrane of a cell (i.e., a "transmembrane domain"). The transmembrane domain of the subject polypeptides comprises the amino acid sequence of the transmembrane domain of wild-type FasL, as described above. In addition, such polypeptides include an amino acid sequence within the cytoplasm of the cell (i.e., the amino terminal "cytoplasmic domain" or "intracellular domain"). Such cytoplasmic domain comprises the amino acid sequence of the cytoplasmic domain of wild-type FasL.

Polypeptides of the invention are capable of specifically interacting with the Fas receptor. By "capable of specifically interacting with the Fas receptor" is meant that the subject polypeptides are capable of at least one of a broad range of specific interactions with the Fas receptor. Included in these specific interactions are the ability to activate the Fas receptor or initiate Fas receptor-mediated signalling pathways, specifically bind to the Fas receptor, or associate or interact with the Fas receptor, both with and without activation, and the like. The term "association" or "associate" means that a subject polypeptide and Fas can bind to each other relatively specifically and thus can form a bound complex. In particular, the association of the subject polypeptide and Fas is sufficiently specific such that the bound complex can form in vivo in a cell or in vitro under suitable conditions (see Examples below). Other methods for determining whether a subject polypeptide can bind Fas (and thus whether the polypeptide constitutes a polypeptide of the invention) are known and include, for example, those assays described in the Examples section below.

The polypeptides are characterized by their ability to affect Fas receptor-mediated pathways or signal cascades. In particular, some polypeptides of the invention are characterized by their ability to activate Fas receptor-mediated pathways, such as apoptosis. By "activate a Fas receptor-mediated pathway" is meant the initiation of a signalling event or cascade within a biological system that is normally initiated by the binding of a ligand to the Fas receptor (i.e., in vivo). The signalling cascade leads to a catabolic or anabolic reaction within a biological system (e.g., cells). Often, the Fas receptor-mediated pathway is apoptosis, and the catabolic reaction is cell death. Activation of Fas-mediated apoptosis generally is determined by known cell death or cell viability assays, such as DNA fragmentation ELISAs or viability staining using, for example, WST-1 staining.

Some polypeptides of the invention are capable of specifically interacting with or binding to the Fas antigen receptor, but incapable of inducing apoptosis. Such polypeptides serve as substances that compete with wild-type FasL expressed on a cell, organ, or tissue for the Fas receptor. Such polypeptides are useful for the purpose of artificially inhibiting or reducing apoptosis.

In addition to their ability to specifically interact with the Fas antigen receptor, the polypeptides of the present invention are also characterized by their structure. In general, the polypeptides of the invention comprise a noncleavable form of FasL. Specifically, the subject polypeptides comprise an extracellular domain of FasL having a modified FasL protease recognition region that inhibits proteolytic cleavage of the polypeptide from a cell membrane relative to proteolytic cleavage of wild-type FasL. Such polypeptides can be characterized by at least two approaches—both of which are discussed in detail below. In brief, in the first approach, the subject polypeptide comprises a FasL protease recognition region having at least one mutation which inhibits, reduces, or prevents action of a protease, such as a matrix metalloprotease or the like. With such a mutation, proteolytic cleavage of all, substantially all, or a portion of the polypeptide from the cell membrane to which it is bound or linked is inhibited, reduced, or prevented relative to proteolytic cleavage of all, substantially all or a portion of wild-type FasL from a cell membrane to which wild-type FasL is bound.

In a second approach, the subject polypeptides comprise an extracellular domain of a wild-type FasL. The domain has a capacity to activate a Fas receptor-mediated pathway. Such polypeptides are linked to a cell membrane by a linker between the extracellular domain and the cell membrane such that on cleavage of FasL with a protease (e.g., a matrix metalloprotease or similar enzyme), the extracellular domain remains linked to the cell membrane. Such a linkage is made by various means; for example, the extracellular domain can be linked via a covalent bond or other bond or linkage to a membrane-anchored moiety in the cell membrane, such as a polypeptide, glycoprotein, or lipid. See. e.g., U.S. patent application Ser. No. 5,109,113, which is incorporated herein by reference in its entirety for all purposes.

Both of these approaches—a polypeptide comprising a mutated FasL protease recognition region or a polypeptide comprising an extracellular FasL domain artificially linked to the cell membrane—provide at least one benefit. For either alternative, conversion of membrane-bound FasL to soluble FasL by proteolytic action is reduced. That is, the polypeptide constitutes a "noncleavable" form of FasL. Consequently, little or no systemic or non-specific cell or tissue injury occurs, as is found with soluble FasL when it is circulated. See. e.g., Nagata et al., *Science*, 267:1449–1456 (1995). As a result, the polypeptides of the invention are of benefit in reducing or eliminating nonspecific or systemic tissue, organ, or cell damage and, moreover, can be of benefit in artificially and selectively modulating apoptosis in a variety of tissues and cells and for use in therapeutic and prophylactic treatment of disorders responsive to the Fas-mediated pathways, such as apoptosis.

In one aspect, the invention provides a polypeptide having a capacity to activate a Fas receptor-mediated pathway and a modified protease recognition region, wherein proteolytic cleavage of all, substantially all or a portion of the polypeptide from the cell membrane to which it is bound or linked (i.e., a first cell membrane) is reduced or inhibited relative to proteolytic cleavage of all, substantially all or a portion of wild-type FasL from the cell membrane to which wild-type FasL is bound (i.e., a second cell membrane). In many instances, the polypeptide resides on the surface of the cell. In most instances, the polypeptide specifically interacts with, associates with, or binds to the Fas receptor. In many instances, the Fas receptor-mediated pathway is apoptosis. For some such polypeptides, the modified FasL protease recognition region is formed by a wild-type FasL protease recognition region having at least one amino acid mutation. Such polypeptides are derived from human FasL or FasL of other species, including mice.

The amino acid sequence of wild-type human FasL (and its nucleic acid sequence that encodes for this amino acid sequence) are well known. See. e.g., Takahashi et al., *Int'l Immunol.* 6:1567–1574 (1994). The amino acid sequence of wild-type, full-length human FasL is shown in SEQ ID NO:1. SEQ ID NO:1 is based on the amino acid sequence for wild-type human FasL as described in Takahashi et al., supra, FIG. 1. (EP Patent Application, Publ. No. 0 675 200 A1, supra, also discloses the full-length amino acid sequence of human FasL.)

Some polypeptides of the invention have a capacity to activate a Fas receptor-mediated pathway and at least 70%, 80%, 85%, or 90% sequence identity with wild-type FasL or an allelic or species variation thereof, or a biologically active fragment thereof, except that the amino acid sequence of such polypeptide differs from the sequence of wild-type FasL by at least one mutation within a FasL protease recognition region within the extracellular domain of wild-type FasL. Such mutation inhibits proteolytic cleavage of the polypeptide from a cell membrane to which the polypeptide is bound or linked (i.e., first cell membrane) relative to proteolytic cleavage of wild-type FasL from a cell membrane to which it is bound (i.e., second cell membrane).

Some polypeptides of the invention have a capacity to activate a Fas receptor-mediated pathway and at least 70%, 80%, 85%, or 90% sequence identity with the sequence of SEQ ID NO:1 or an allelic or species variation thereof, or a biologically active fragment thereof, except that the amino acid sequence of such polypeptide differs from the sequence of SEQ ID NO:1 by at least one mutation within a FasL protease recognition region within the extracellular domain of SEQ ID NO:1. Such mutation inhibits proteolytic cleavage of the polypeptide from a cell membrane to which the polypeptide is bound or linked (i.e., first cell membrane) relative to proteolytic cleavage of SEQ ID NO:1 from a cell membrane to which SEQ ID NO:1 is bound (i.e., second cell membrane).

The subject polypeptide comprises a full-length human FasL, as shown in SEQ ID NO:1 (or an allelic or species variant thereof or biologically active fragment thereof), with at least one amino acid mutation within the FasL protease recognition region, including those specific mutations described below. Such mutations also occur outside the protease recognition region or protease cleavage region (also known as "protease cleavage site"), but within the extracellular domain of FasL such that they interfere with or affect conformation of the protease recognition region sequence. In many instances, the polypeptide resides on the surface of the cell. In most instances, the polypeptide specifically interacts with, associates with, or binds to the Fas receptor. In many instances, the Fas receptor-mediated pathway is apoptosis.

In some embodiments, such polypeptides have at least 80 percent sequence identity, at least 90 percent sequence identity, or preferably at least 95 percent sequence identity or more (e.g., 99 percent sequence identity) with the amino acid sequence of SEQ ID NO:1 (or an allelic or species variation thereof or biologically active fragment thereof), except that the amino acid sequence of the polypeptide differs from the sequence of SEQ ID NO:1 by at least one mutation within the FasL protease recognition region of SEQ ID NO:1 which serves to inhibit proteolytic cleavage of the polypeptide from the cell membrane relative to cleavage of SEQ ID NO:1 from a second cell membrane. As noted above, the extracellular domain of human FasL comprises the amino acid sequence of from the 103rd amino acid residue to the 281st amino acid residue of full-length FasL (SEQ ID NO:1).

The mutations of the FasL protease recognition region of the extracellular domain of the subject polypeptides are selected according to several constraints. First, such mutations substantially or completely inhibit, reduce, or prevent proteolytic cleavage of substantially all or a portion of the subject polypeptide from the cell membrane with which it is associated without reducing or affecting the capacity of the polypeptide to activate a Fas receptor-mediated pathway, such as apoptosis.

Second, such mutations do not substantially inhibit or affect the manner in which the polypeptide interacts with or binds to a Fas receptor. In other words, a polypeptide of the invention having a mutated FasL protease recognition region has substantially the same binding affinity for a Fas receptor (e.g., within a factor of 2 or 10) as it would for a naturally occurring (i.e., wild-type) FasL protease recognition region. Nor should a mutation within the FasL protease recognition region affect the specificity of binding of the polypeptide comprising the mutated FasL protease recognition region to the Fas receptor (e.g, a polypeptide bearing a mutated FasL protease recognition region should compete for binding to a Fas receptor with an unmutated form of FasL).

Third, the mutation does not perturb the structure of the FasL protease recognition region so far from that of the wild-type FasL protease recognition region as to result in decreased apoptotic signal transduction. Thus, polypeptides of the invention bearing mutated FasL protease recognition regions are useful for inducing apoptosis. Furthermore, such polypeptides are useful in therapeutic and prophylactic methods for alleviating symptoms of patients suffering from disorders characterized by inadequate or inappropriate stimulation or action of the Fas receptor-mediated pathway in cells, tissues, or organs of such patients, including, for example, inappropriate stimulation or activation of a Fas receptor-mediated pathway mediated by soluble FasL.

Mutations within the extracellular domain of FasL, and most notably within the protease recognition region of FasL, typically result in a loss of recognition of FasL by a protease. Such mutations are produced by methods well known in the art, including by the methods outlined in the Examples below. A mutant FasL protease recognition region can be obtained, for example, by site-directed mutagenesis of a nucleic acid molecule encoding a FasL protease recognition region and screening the mutagenized nucleic acid molecules to identify a nucleic acid molecule that expresses a FasL that is noncleavable and can specifically interact with or bind Fas. The mutation comprises a deletion of at least one amino acid residue from an amino acid sequence of the FasL protease recognition region. Alternatively, the mutation comprises the substitution of at least one amino acid residue in an amino acid sequence of the FasL protease recognition region. In another aspect, the mutation comprises the insertion of at least one additional amino acid residue into an amino acid sequence of the FasL protease recognition region. In addition, the mutation comprises any combination of the three above-specified mutations.

Such mutations are typically made within the extracellular domain of human FasL, and more typically, within the FasL protease recognition region. Given that human FasL is a TNF-related protein and that the metalloprotease cleavage site of human TNF-α has been precisely determined by sequencing the terminal amino acid of soluble TNF-α (see Kriegler et al., *Cell* 53:45–53 (1988), the protease recognition and cleavage site(s) of FasL can be postulated based on comparisons between the known amino acid sequences of human TNF-α and human FasL.

The amino acid sequence of the metalloprotease recognition region of human TNFα is shown in FIG. 1. This recognition region comprises an amino acid sequence comprising at least amino acid residue 64 to amino acid residue 97 of full-length human TNF-a. Perez et al. performed a series of deletions in human TNFα in an attempt to create a noncleavable, functional form of TNF-α. Perez et al., *Cell* 63:251–258 (1990). The amino acid deletion that resulted in noncleavable, functional form of human TNF-α is shown in FIG. 1 in bold. See id.

It is known that cleavage of the 40-kDa membrane-bound form of human FasL produces a 26-kDa soluble form of FasL. Based on the size of soluble FasL, as well as sequence comparisons with the well-defined cleavage sites of human TNF-α, it is postulated that at least one mutation between residue 118 and residue 155 of SEQ ID NO:1 satisfies the specified criteria for the mutations discussed above. Thus, in one aspect, the invention provides polypeptides having at least 70%, 80%, 85%, or 90% sequence identity with the sequence of SEQ ID NO:1 (or an allelic or species variation thereof or biologically active fragment thereof) and a capacity to activate a Fas receptor-mediated pathway, wherein the amino acid sequence of the polypeptide differs from the sequence of SEQ ID NO:1 (or allelic or species variation thereof) by the deletion of at least one amino acid residue between residue 118 and residue 155 of SEQ ID NO:1, such that the mutation inhibits proteolytic cleavage of the polypeptide from a cell membrane to which it is bound or linked (i.e., a first cell membrane) relative to proteolytic cleavage of SEQ ID NO:1 from a cell membrane to which SEQ ID NO:1 is bound (i.e., a second cell membrane). Also provided are allelic or species variations of such polypeptides, or biologically active fragments thereof.

In another embodiment, the invention provides a polypeptide that is otherwise identical to that specified above, but in which the mutation comprises substitution of at least one amino acid residue between residue 118 and residue 155 of SEQ ID NO:1, or an allelic or species variation thereof or biologically active fragment thereof, with a different amino acid residue (including any of the 20 usual amino acids or modifications thereof. Such amino acid substitution may or may not be conservative by the classification of amino acids described above. Such substitutions may or may not introduce substantial changes in charge distribution or conformation of the FasL protease constant region containing them.

In yet another embodiment, the invention provides a polypeptide that is identical to that specified above, but in which the mutation comprises insertion of at least one additional amino acid residue (including any of the 20 usual amino acids or modifications thereof) between residue 118 and residue 155 of SEQ ID NO:1, or an allelic or species variation thereof or biologically active fragment thereof.

In one aspect, the invention provides polypeptides as described above having at least 70%, 80%, 85%, or 90% sequence identity with the sequence of SEQ ID NO:1 and a capacity to activate a Fas receptor-mediated pathway, wherein the amino acid sequence of the polypeptide differs from the sequence of SEQ ID NO:1 by the deletion of at least five amino acid residues between residue 125 and residue 146 of SEQ ID NO:1, or an allelic or species variation thereof or biologically active fragment thereof. Such mutation inhibits proteolytic cleavage of the polypeptide from the cell membrane relative to proteolytic cleavage of SEQ ID NO:1 from a second cell membrane. In some instances, such at least five amino acid residues are contiguous. In one embodiment, the mutation comprises deletion of amino acid residue 126 to amino acid residue 135 of SEQ ID NO:1 or an allelic or species variation thereof or biologically active fragment thereof. In another embodiment, the mutation comprises deletion of amino acid residue 126 to amino acid residue 145 of SEQ ID NO:1, or an allelic or species variation thereof or biologically active fragment thereof.

The polypeptides of the present invention are generally characterized by their structural relation to deletion mutant 2 (also known as "mutant delta 2"or "Del 2"), which comprises SEQ ID NO:1 (or an allelic or species variation thereof or biologically active fragment thereof) from which amino acid residues 126 to 135 have been deleted. See FIG. 1. Such polypeptides will have an amino acid sequence that is substantially homologous to the amino acid sequence of mutant 2, or biologically active fragments thereof. In a still more preferred aspect, the subject polypeptides will comprise SEQ ID NO:1 with amino acid residues 126 to 135 of SEQ ID NO:1 (or an allelic or species variation thereof or biologically active fragment thereof) deleted, or conservative substitutions thereof.

In another embodiment, the polypeptides of the present invention are characterized by their structural relation to deletion mutant 3 (also known as "mutant delta 3"or "Del 3"), which comprises SEQ ID NO:1 (or an allelic or species variation thereof or biologically active fragment thereof) from which amino acid residues 126 to 145 have been deleted. See FIG. 1. In yet another embodiment, the subject polypeptides comprise an amino acid sequence that is substantially homologous to the amino acid sequence of mutant 3, or biologically active fragments thereof. In an alternative embodiment, the subject polypeptides comprise SEQ ID NO:1 (or an allelic or species variation thereof or biologically active fragment thereof) from which amino acid residues 126 to 145 of SEQ ID NO:1 deleted, or conservative substitutions thereof.

In one embodiment, where the subject polypeptide comprises an extracellular domain of a wild-type FasL having a capacity activate a Fas receptor-mediated pathway, said polypeptide being linked to a cell membrane by a linker between the domain and the membrane such that on cleavage of FasL with a protease the domain remains linked to the membrane, the polypeptide comprises a sequence that is substantially homologous to the amino acid sequence of wild-type FasL or to SEQ ID NO:1, or an allelic or species variation thereof or biologically active fragment thereof. In another aspect, such polypeptide comprises a sequence having at least 70%, 80%, 15 85%, or 90% sequence identity with the sequence of wild-type FasL or the sequence shown in SEQ ID NO:1, or with an allelic or species variation thereof or biologically active fragment thereof.

Biologically active fragments of the polypeptides of the invention will generally be useful where use of a full-length protein is unsuitable for the particular application. Such applications include modelling of analogs, mimics, or small molecules, or therapeutic applications where administration of larger polypeptides is impracticable. In general, biologically active fragments of the above-described polypeptides and proteins include any sub-sequence of the polypeptides of the invention, including those described herein as mutant 1, mutant 2, or mutant 3. Such fragments will generally comprise at least about 3 to about 1000 contiguous amino acids. Typically, these peptides will comprise from at least about 5 to about 500 amino acids in length. More typically, these peptides will comprise from at least about 10 to about 500 amino acids in length, even more typically at least about 10 to about 250 amino acids in length, and preferably at least about 20 to about 200 amino acids in length. Generally, the length of the fragment depends, in part, upon the application for which the particular peptide is to be used. For example, for raising antibodies, the peptides can be of a shorter length, for example, from about 5 to about 50 amino acids in length, whereas for binding or binding inhibition applications, the peptides will generally have a greater length, for example, from about 10 to about 1000 amino acids in length, preferably, from about 20 to about 500 amino acids in length, and more preferably, from about 20 to about 200 amino acids in length.

Selection of biologically active peptide fragments of the sequence shown in FIG. 1 are generally carried out by the methods described herein. For example, selective proteolytic digestion, recombinant deletional methods, or de novo peptide synthesis methods may be employed to identify portions of the above-described polypeptides that possess the desired biological activity (e.g., Fas receptor binding, inhibition of Fas receptor/FasL interaction, activation of Fas receptor-mediated apoptosis). See. e.g., *Molecular Cloning, A Laboratory Manual*, Vols. 1–3 (Cold Spring Harbor Laboratory, Cold Spring Harbor, N.Y., 2nd ed. 1989). Once such fragments are generated, they are then assayed to determine if they possess the desired biological activity. For example, such fragments may be screened for their ability to bind Fas receptor by blotting the fragment on a solid support (e.g., nitrocellulose, PVDF, etc.). and probing the fragment with labelled Fas to identify fragments to which the Fas receptor binds. Alternatively, the fragments may be screened in a cell death assay to determine if the fragment possesses the capability to activate Fas receptor-mediated cell death or apoptosis.

The term "substantially homologous" when referring to polypeptides refers comparatively to two amino acid sequences which, when optimally aligned, are at least about 75% homologous, preferably at least about 80% homologous, more preferably at least about 85% homologous, even more preferably at least about 90% homologous, and still more preferably at least about 95% homologous. Optimal alignment of sequences for aligning a comparison window may be conducted by the local homology algorithm of Smith and Waterman, *Adv. Appl. Math.* 2:482 (1981), by the homology alignment algorithm of Needleman and Wunsch, *J. Mol. Biol.* 48:443 (1970), by the search for similarity method of Pearson and Lipman, *Proc. Natl. Acad. Sci. (USA)* 85:2444 (1988), or by computerized implementations of these algorithms (e.g., GAP, BESTFIT, FASTA, and TFASTA in the Wisconsin Genetics Software Package Release 7.0, Genetics Computer Group, 575 Science Dr., Madison, Wis.).

As noted above, the polypeptides of the present invention are generally prepared by using recombinant or synthetic methods that are well known in the art. Recombinant techniques are generally described in Sambrook et al., *MOLECULAR CLONING, A LABORATORY MANUAL* (Cold Spring Harbor Laboratory, Cold Spring Harbor, N.Y., 2nd ed. 1989). Techniques for the synthesis of polypeptides are generally described in Merrifield, *J. Amer. Chem. Soc.* 85:2149–2456 (1963), Atherton et al., *SOLID PHASE PEPTIDE SYNTHESIS: A PRACTICAL APPROACH* (IRL Press 1989), and Merrifield, *Science* 232:341–347 (1986). In one aspect, the polypeptides of the present invention are expressed by a suitable host cell that has been transfected with a nucleic acid of the invention, as described in greater detail below.

Isolation and purification of the polypeptides of the present invention can also be carried out by methods that are generally well known in the art. For example, the polypeptides are purified using readily available precipitation or chromatographic methods (e.g, ion exchange, hydrophobic interaction, high-pressure liquid chromatography ("HPLC") or affinity chromatography) to achieve the desired purity. As described above, such polypeptides are typically attached, bound, coupled to, or linked to a cell membrane and substantially noncleavable from the membrane relative to wild-type FasL, as described herein. Affinity chromatography is particularly attractive in allowing an individual to take advantage of a specific biological activity of the desired polypeptide (e.g., Pas receptor binding, activation of Pas receptor-mediated pathway, inducement of apoptosis, presence of antigenic determinants, or the like). The mutated or modified FasL polypeptides of the invention may be purified, for example, by affinity chromatography using widely available antibodies which bind outside the mutated or modified region of FasL. Alternatively, one could add monoclonal antibody tag or a hexahistidine tail at the C terminus or N terminus of the subject polypeptide and employ either immunity chromatography using monoclonal antibodies directed at the tag or a nickel chromatography column which binds the hexahistidine tail of the polypeptide by affinity chromatography. Purified FasL polypeptides can be used to produce monoclonal antibodies to the modified or mutated FasL protease recognition region. Polypeptides of the invention may be precipitated by using monoclonal antibodies that specifically recognize the mutated or modified FasL protease recognition region or recognize the extracellular domain of the polypeptide that is linked to the cell membrane by a linker. Briefly, antibodies to the mutated FasL protease recognition region or to the extracellular domain which is linked to a cell membrane by a linker may be coupled to a suitable solid support and contacted with a mixture of proteins containing the polypeptides of the invention under conditions conducive to the association of these polypeptides with the antibody. Once bound to the immobilized antibody, the solid support is washed to remove unbound material and/or nonspecifically bound proteins. The desired polypeptides are then eluted from the solid support in substantially pure form by, for example, a change in salt, pH, or buffer concentration. Suitable solid supports for affinity purifications are well known in the art and are generally commercially available from, for example, Pharmacia, Inc. or Sigma Chemical Company. Examples of such solid supports include agarose, cellulose, dextran, silica, polystyrene, or other similar solid supports.

In addition to those polypeptides and fragments described above, the present invention also provides fusion proteins which contain these polypeptides or fragments. The term "fusion protein" generally refers to a composite protein—that is, a single contiguous amino acid sequence, made up of two distinct, heterologous polypeptides that are not normally fused together in a single amino acid sequence. Thus, a fusion protein includes a single amino acid sequence that contains two entirely distinct amino acid sequences or two similar or identical polypeptide sequences, provided that these sequences are not normally found together in a single amino acid sequence. Fusion proteins are generally prepared using either recombinant nucleic acid methods, i.e., as a result of transcription and translation of a gene fusion, which fusion comprises a segment encoding a polypeptide of the invention and a segment encoding a heterologous protein, or by chemical synthesis methods well known in the art.

In one aspect, the polypeptides of the invention are provided as a fusion protein, wherein the first component comprises a polypeptide having a capacity to activate a Fas receptor-mediated pathway and at least 70%, 80%, 85%, or 90% sequence identity with the amino acid sequence of SEQ ID NO:1 (or allelic or species variation thereof or biologically active fragment thereof), except that such sequence differs from that of SEQ ID NO:1 by at least one mutation within a FasL protease recognition region within SEQ ID NO:1. Such mutation inhibits or reduces proteolytic cleavage of the polypeptide from the cell membrane as compared to the proteolytic cleavage of SEQ ID NO:1 (e.i., wild-type FasL) from a cell membrane to which SEQ ID NO:1 is bound.

For some such polypeptides, the first component is fused to a second component, which typically comprises a heterologous protein linked to a membrane of the cell. The heterologous protein is linked to a component within the cell membrane (e.g., polypeptide or lipid) via a covalent bond or is incorporated into the cell membrane, such as, for example, a membrane protein. In some proteins, the first component of the fusion protein is fused directly with a transmembrane segment of such a heterologous protein.

Also included within the present invention are amino acid variants of the above-described polypeptides. These variants may include insertions, deletions, and substitutions with other amino acids. For example, in some aspects, conservative amino acid substitutions are made—that is, substitution of selected amino acids with different amino acids having similar structural characteristics (e.g, net charge, hydrophobicity, and the like). Glycosylation modifications, either changed, increased amounts, or decreased amounts, as well as other sequence modifications are also envisioned.

Systematic substitution of one or more amino acids of a consensus sequence with a D-amino acid of the same type (e.g., D-lysine in place of L-lysine) may also be used to generate more stable polypeptides. In addition, constrained polypeptides comprising a consensus sequence or a substantially identical consensus sequence variation may be generated by methods known in the art (Rizo and Gierasch, *Ann. Rev. Biochem.* 61:387 (1992) by, for example, adding internal cysteine residues capable of forming intramolecular disulfide bridges which cyclize the polypeptide. Similarly, modification of the amino or carboxy terminals may also be used to confer stabilizing properties upon the polypeptides of the invention (e.g, amidation of the carboxy-terminus or acylation of the amino-terminus). In addition, substitution of amino acids involved in the activation of the Fas receptor can be used to generate dominant negative inhibitors of FasL/Fas receptor interactions.

Although the peptides of the invention are primarily described using the term of "peptide" or "peptides," these terms also include structural analogs and derivatives of the above-described peptides (e.g., peptides having conservative amino acid insertions, deletions or substitutions, peptidomimetics and the like). For example, in addition to the above-described peptides, which comprise naturally-occurring amino acids, peptidomimetics of the peptides of the present invention are also provided. Peptide analogs are commonly used in the pharmaceutical industry as non-peptide drugs with properties analogous to those of the template peptide. These types of non-peptide compounds are termed "peptide mimetics" or "peptidomimetics" and are usually developed with the aid of computerized molecular modeling. Fauchere, *Adv. Drug Res.* 15:29 (1986); Veber and Freidinger, *TINS* 392 (1985); and Evans et al., *J. Med. Chem.* 30:1229 (1987). Peptide mimetics that are structurally similar to therapeutically or prophylactically useful peptides may be used to produce an equivalent therapeutic or prophylactic effect. Generally, peptidomimetics are structurally similar to a paradigm peptide (i.e., a peptide that has a biological or pharmacological activity), such as naturally-occurring peptide having potassium channel opener activity, but have one or more peptide linkages optionally replaced by a linkage selected from the group consisting of: $—CH_2NH—$, $—CH_2S—$, $—CH_2—CH_2—$, $—CH{=}CH—$ (cis and trans), $—COCH_2—$, $—CH(OH)CH_2—$, and $—CH_2SO—$. Such peptidomimetics may be generated by methods known in the art and further described in the following references: Spatola, A. F., "Peptide Backbone Modifications" in *CHEMISTRY AND BIOCHEMISTRY OF AMINO ACIDS, PEPTIDES, AND PROTEINS*, Vol. 7, 267 (Boris Weinstein ed. 1983); Morley, *Trends Pharm Sci.* 463–468 (1980) (general review); Hudson et al., *Int. J. Pept. Prot. Res.* 14:177–185 (1979) ($CH_2NH—$, $CH_2CH_2—$);

Spatola et al., *Life Sci.* 38:1243–1249 (1986) (—CH$_2$—S); Hann, *J. Chem. Soc. Perkin Trans.* I 307–314 (1982) (—CH—CH—, cis and trans); Almquist et al., *J. Med. Chem.* (1980) 23:1392–1398 (—COCH$_2$—); Jennings-White et al., *Tetrahedron Lett.* 23:2533 (1982) (—COCH$_2$—); Szelke et al., European Appln. EP 45665 (1982) CA: 97:39405 (1982) (—CH(OH)CH$_2$—); Holladay et al., *Tetrahedron Lett.* 24:4401–4404 (1983) (—C(OH) CH$_2$—); and Hruby, *Life Sci.* 31:189–199 (1982) (—CH$_2$—S—).

Peptide mimetics may have significant advantages over peptide embodiments, including, for example: more economical production; greater chemical stability; enhanced pharmacological properties (half-life, absorption, potency, efficacy, etc.); altered specificity (e.g., a broad-spectrum of biological activities); reduced antigenicity; and others.

For some applications, it is desirable to provide the peptides of the invention as labeled entities (i.e., covalently attached or linked to a detectable group, to facilitate identification, detection and quantification of the peptide in a given circumstance). These detectable groups comprise a detectable protein group (e.g., an assayable enzyme or antibody epitope as described above in the discussion of fusion proteins). Alternatively, the detectable group is selected from a variety of other detectable groups or labels, such as radiolabels (e.g., $^{125}$I, $^{32}$P, or $^{35}$S) or a chemiluminescent or fluorescent group. Similarly, the detectable group is a substrate, cofactor, inhibitor, or affinity ligand. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the molecules to which the peptidomimetic binds (e.g., Fas receptor) to produce the therapeutic effect. Derivatization (e.g., labelling) of peptidomimetics should not substantially interfere with the desired biological or pharmacological activity of the peptidomimetic. Generally, peptidomimetics of peptides of the invention bind to the Fas receptor with high affinity and/or possess detectable biological activity (i.e., ability to activate one or more Fas receptor-mediated phenotypic changes; ability to induce apoptosis).

III. Nucleic Acids of the Invention

In another aspect, the present invention provides nucleic acids which encode the polypeptides of the invention, as well as expression vectors that include these nucleic acids, and cell lines and organisms that are capable of expressing these nucleic acids. These nucleic acids, expression vectors and cell lines are generally used to produce the polypeptides of the invention. In general, the isolated nucleic acids of the present invention encode a polypeptide comprising a non-cleavable form of FasL and having a capacity to activate a Fas receptor-mediated pathway. In one aspect, such nucleic acids encode a polypeptide having the capacity to activate a Fas receptor-mediated pathway and comprising a wild-type FasL protease recognition region having at least one mutation such that proteolytic cleavage of all, substantially all or a portion of the polypeptide from the cell membrane is reduced relative to proteolytic cleavage of all, substantially all or a portion of wild-type FasL from a cell membrane to which it is bound. In some instances, such mutation occurs within the extracellular domain of FasL, but outside the protease recognition region.

Wild-type, full-length human FasL is represented by the amino acid sequence shown in SEQ ID NO:1. A nucleic acid sequence that codes for SEQ ID NO:1 is shown in SEQ ID NO:2. SEQ ID NO:2 is based on the nucleic acid sequence for human FasL as described in Takahashi et al., supra (FIG. 1), with the exception that the non-coding nucleotides shown in Takashi (e.g., introns) have been eliminated.

In one aspect, the nucleic acids encode a polypeptide having at least 70%, 80%, 85%, or 90% sequence identity with the amino acid sequence of wild-type FasL, or an allelic or species variation thereof or biologically active fragment thereof, and a capacity to activate a Fas receptor-mediated pathway, except that the amino acid sequence differs from the sequence of wild-type FasL by at least one mutation within the FasL protease recognition region within wild-type FasL. The mutation inhibits or reduces proteolytic cleavage of the polypeptide from a cell membrane to which it is bound or linked relative to proteolytic cleavage of wild-type FasL (or the allelic or species variation or biologically active fragment thereof) from another cell membrane to which wild-type FasL (or the allelic or species variation or biologically active fragment thereof) is bound.

In yet another aspect, the nucleic acids encode a polypeptide having at least 70%, 80%, 85%, or 90% sequence identity with the amino acid sequence of SEQ ID NO:1 (or an allelic or species variation thereof or biologically active fragment thereof) and a capacity to activate a Fas receptor-mediated pathway, except that the amino acid sequence differs from the subject sequence of SEQ ID NO:1 by at least one mutation within the FasL protease recognition region within SEQ ID NO:1. The mutation inhibits or reduces proteolytic cleavage of the polypeptide from a cell membrane to which it is bound or linked relative to proteolytic cleavage of SEQ ID NO:1 (or the allelic or species variation or biologically active fragment thereof) from another cell membrane to which SEQ ID NO:1 (or the allelic or species variation or biologically active fragment thereof) is bound.

The mutation may comprise any of those discussed herein. For example, the mutation may comprise the deletion, substitution, or insertion of at least one amino acid residue between residue 118 and residue 155 of SEQ ID NO:1, or an allelic or species variation thereof or biologically active fragment thereof. In an alternative embodiment, the mutation comprises deletion of at least five amino acid residues between residue 125 and residue 146 of SEQ ID NO:1 or an allelic or species variation thereof or biologically active fragment thereof. In one aspect, the five amino acid residues that are deleted are contiguous.

In another embodiment, such mutation comprises deletion of amino acid residue 126 to amino acid residue 135 of SEQ ID NO:1, or some combination thereof. In still another embodiment, such mutation comprises deletion of amino acid residue 126 to amino acid residue 145 of SEQ ID NO:1, or some combination thereof.

Nucleic acids of the present invention include RNA, cDNA, genomic DNA, synthetic forms and mixed polymers, both sense and antisense strands. Different alleles of each isoform are also included. The present invention also provides recombinant nucleic acids which are not otherwise naturally occurring or wild-type nucleic acids. The nucleic acids described herein also include self replicating plasmids and infectious polymers of DNA or RNA. Unless specified otherwise, conventional notation for nucleic acids is used herein. For example, as written, the left-hand end of a single stranded polynucleotide sequence is the 5'-end, whereas the right-hand end is the 3'-end. The left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

The nucleic acids of the present invention are present in whole cells, cell lysates, or in partially pure or substantially pure or isolated form. When referring to nucleic acids, the terms "substantially pure" or "isolated" generally refer to the nucleic acid separated from contaminants with which it is generally associated (e.g., lipids, proteins, and other nucleic acids). The substantially pure or isolated nucleic acids of the present invention are generally greater than about 50% pure. Typically, these nucleic acids are more than about 60% pure, usually, from about 75% to about 85% pure, more typically about 90% pure, and preferably from about 95% to about 98% pure.

The DNA compositions generally include a coding region which encodes a polypeptide that is capable of activating a Fas receptor-mediated pathway and/or binding to Fas receptor, and that is noncleavable or substantially noncleavable from the cell membrane to which is it bound or linked. Such nucleic acids or fragments thereof comprise part or all of the cDNA sequence that encodes the polypeptides of the present invention. Some nucleic acids will typically encode an amino acid sequence which is substantially homologous to SEQ ID NO:1, or biologically active fragments thereof.

The phrase "nucleic acid sequence encoding" refers to a nucleic acid which directs the expression of a specific protein or polypeptide. The nucleic acid sequences include both the DNA strand sequence that is transcribed into RNA and the RNA sequence that is translated into protein. The nucleic acid sequences include both the full-length nucleic acid sequences as well as non full-length sequences derived from the full-length sequence. It should be further understood that the sequence includes the degenerate codons of the native sequence or sequences which may be introduced to provide codon preference in a specific host cell.

Two nucleic acids share sequence "identity" or "homology" if the two nucleic acids or designated segments thereof, when optimally aligned with appropriate nucleotide insertions or deletions, are identical in at least about 50% of the nucleotides. The term "substantial homology" in the nucleic acid context means that the nucleic acids or their complementary strands, when compared, are identical when optimally aligned with appropriate nucleotide insertions or deletions, in at least about 60% of the nucleotides, typically at least about 70%, usually at least about 80%, more usually at least about 85%, preferably at least about 90%, and more preferably at least about 95 to 98% of the nucleotides. Alternatively, substantial homology exists when the segments will hybridize under selective hybridization conditions, to a strand, or its complement, using a sequence derived from the nucleic acids of the invention.

Selectivity of hybridization exists when hybridization occurs with a certain degree of specificity rather than being random. Typically, selective hybridization will occur when there is at least about 55% homology over a stretch of at least about 14 nucleotides, preferably at least about 65%, more preferably at least about 75%, more preferably at least about 80 even more preferably at least about 85 and most preferably at least about 90%. See Kanehisa, *Nuc. Acids Res.*, 12:203–213 (1984). Selective hybridization exists when hybridization occurs which is more selective than that seen for nucleic acids displaying nonspecific interactions, i.e., are wholly unrelated. See Kanehisa, *Nucleic Acid Res.* 12:203–213 (1984). Examples of such selective hybridization conditions include, for example, hybridization under the hybridization and wash conditions of 50% formamide at 42° C. Other stringent hybridization conditions may also be selected. Generally, stringent conditions are selected to be about 5° C. lower than the thermal melting point ($T_m$ for the specific sequence at a defined ionic strength and pH. The $T_m$ is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may significantly affect the stringency of hybridization, including, among others, base composition and size of the complementary strands, the presence of organic solvents and the extent of base mismatching, the combination of parameters is more important than the absolute measure of any one.

There are various methods of isolating the nucleic acids which may be used to prepare nucleic acids encoding polypeptides of the present invention (e.g., by deleting, via site-directed mutagenesis, specific codons of wild-type FasL), including those described in the Examples below. Typically, DNA is isolated from a genomic or cDNA library using labeled oligonucleotide probes specific for sequences in the desired DNA. Restriction endonuclease digestion of genomic DNA or cDNA containing the appropriate genes can be used to isolate the desired DNA. A panel of restriction endonucleases can be constructed to give cleavage of the DNA in desired regions, i.e., to obtain segments from which nucleotide sequences encoding biologically active fragments of the polypeptides of the invention can be prepared. Following restriction endonuclease digestion, DNA encoding the polypeptides of the invention is identified by its ability to hybridize with a nucleic acid probe in, for example, a Southern blot format. These regions are then isolated using standard methods. See, e.g., Sambrook et al., supra.

PCR methods can also be used to prepare nucleic acids which encode the polypeptides of the present invention. PCR technology is used to amplify specific nucleic acid sequences of the desired nucleic acid (e.g., the DNA which encodes the polypeptides of the invention, directly from MRNA, cDNA, or genomic or cDNA libraries). For example, DNA encoding full-length FasL is isolated from appropriate tissue libraries and PCR amplifying specific portions (e.g., amplifying the entire FasL nucleotide sequence except those nucleic acids to be deleted, as in the mutant forms described above), or as otherwise desired.

Alternatively, solid phase oligonucleotide synthesis methods are also employed to produce the nucleic acids described herein. Such methods include the phosphoramidite method described by, for example, Beaucage and Carruthers, *Tetrahedron Lett.* 22:1859–1862 (1981), or the triester method according to Matteucci et al., *J. Am. Chem. Soc.*, 103:3185 (1981). A double-stranded fragment is then obtained, if desired, by annealing the chemically synthesized single strands together under appropriate conditions or by synthesizing the complementary strand using DNA polymerase with an appropriate primer sequence.

Appropriate primers and probes for amplifying the nucleic acids described herein are generated from analysis of the nucleic acid sequences described herein.

Briefly, oligonucleotide primers complementary to the two 3' borders of the DNA region to be amplified are synthesized. The PCR is then carried out using the two primers. See, e.g., *PCR PROTOCOLS: A GUIDE TO METHODS AND APPLICATIONS* (Innis et al. eds., 1990). Primers can be selected to amplify a variety of different sized segments from the nucleic acid sequence.

The present invention also includes fragments of the above-described nucleic acids. Such fragments will typically comprise a segment of from at least about 10 to about 150 nucleotides, more typically at least about 50 to 200 nucleotides. These fragments are useful to encode the polypeptides of the invention or biologically active 10 fragments thereof, as described herein. Fragments of at least about 10 nucleotides are generally used in site-directed mutagenesis described herein. Also provided are substantially similar nucleic acid sequences, allelic variations, and natural or induced sequences of the above-described nucleic acids. Also included are chemically modified and substituted nucleic acids, e.g., those which incorporate modified nucleotide bases or which incorporate a labelling group.

In addition to comprising a segment which encodes one or more of the above-described polypeptides or biologically active fragments thereof, the nucleic acids of the present invention also comprise a segment encoding a heterologous protein, such that the gene is expressed to produce the two proteins as a fusion protein, as substantially described above.

Usually, the nucleic acids of the present invention will be used in expression vectors for the preparation of the polypeptides described above, i.e., in the production of cell lines that are capable of producing and expressing the heterologous polypeptides of the invention. By "heterologous polypeptides" is meant a polypeptide that is not naturally produced and expressed by the particular host cell. The phrase "expression vector" generally refers to nucleotide sequences that are capable of affecting expression of a structural gene in hosts compatible with such sequences. These expression vectors typically include at least a suitable promoter sequence and, optionally, transcription termination signals. Additional factors necessary or helpful in effecting expression may also be used as described herein.

DNA encoding the polypeptides of the present invention will typically be incorporated into DNA constructs capable of introduction into and expression in an in vitro cell culture. Often, the nucleic acids of the present invention are used to produce a suitable recombinant host cell. Specifically, DNA constructs will be suitable for replication in a cultured mammalian cell line or primary cell cultures. DNA constructs prepared for introduction into a particular host (e.g., mammalian cell lines, such as an endocrine cell) will typically include a replication system recognized by the host, the intended DNA segment encoding the desired polypeptide, and transcriptional and translational initiation and termination regulatory sequences operably linked to the polypeptide encoding segment. A DNA segment is operably linked when it is placed into a functional relationship with another DNA segment. For example, a promoter or enhancer is operably linked to a coding sequence if it stimulates the transcription of the sequence. DNA for a signal sequence is operably linked to DNA encoding a polypeptide if it is expressed as a preprotein that participates in the secretion of the polypeptide. Generally, DNA sequences that are operably linked are contiguous and, in the case of a signal sequence, both contiguous and in reading phase. However, enhancers need not be contiguous with the coding sequences whose transcription they control. Linking is accomplished by ligation at convenient restriction sites or at adapters or linkers inserted in lieu thereof. The selection of an appropriate promoter sequence will generally depend upon the host cell selected for the expression of the DNA segment. Examples of suitable promoter sequences include prokaryotic, and eukaryotic promoters well known in the art. See. e.g., Sambrook et al., supra. The transcriptional regulatory sequences will typically include a heterologous enhancer or promoter which is recognized by the host. The selection of an appropriate promoter will depend upon the host, and are generally well known and available. See Sambrook et al., supra.

Conveniently available expression vectors, which include the replication system and transcriptional and translational regulatory sequences together with the insertion site for the polypeptide encoding segment, may be employed. Examples of workable combinations of cell lines and expression vectors are described in Sambrook et al., supra, and Metzger et al., *Nature* 334:31–36 (1988). For example, suitable expression vectors are expressed in, for example mammalian cells, such as endocrine cells, COS-7 cells, dendritic cells or other antigen-presenting cells, lymphocytes or other cells of lymphoid origin, hemopoietic stem cells or cells of hemopoietic origin, neuronal cells, or embryonic stem cells, by providing constructs for expression in mammalian cells, e.g., pCI-neo vector (available from Promega, Inc.). These constructs typically include the subject nucleic acids and employ an appropriate enhancer/promoter region. A wide variety of expression vectors suitable for such expression are commercially available from, e.g., Promega, Invitrogen, Pharmingen, and the like.

In one aspect, the invention provides vectors containing a nucleic acid sequence encoding a polypeptide having at least 70%, 80%, 85%, or 90% sequence identity with the amino acid sequence of SEQ ID NO:1 and a capacity to activate a Fas receptor-mediated pathway, said amino acid sequence differing from the sequence of SEQ ID NO:1 by at least one mutation within a FasL protease recognition region within SEQ ID NO:1, such that the mutation inhibits proteolytic cleavage of the polypeptide from a cell membrane to which the polypeptide is bound or linked (i.e., first cell membrane) relative to proteolytic cleavage of SEQ ID NO:1 from a cell membrane to which SEQ ID NO:1 is bound (i.e., second cell membrane).

In another aspect, nucleic acids of the invention are generally used in the production of recombinant cell lines that are capable of expressing the polypeptides of the present invention. The invention provides isolated host cells containing a nucleic acid sequence that encodes a polypeptide of the invention, as described above. Such host cells comprise various mammalian cells, such as those described above. With such cells, the expressed polypeptide typically resides on the surface of the cell. Such cells are useful in therapeutic and prophylactic methods for alleviating symptoms of patients suffering from disorders distinguished by inadequate or inappropriate stimulation or action of a Fas receptor-mediated pathway, including inappropriate stimulation or action mediated or caused by soluble FasL, as described below. In brief, such methods comprising delivering to the tissue or organ of the patient an effective amount of a cell containing a nucleic acid sequence encoding a polypeptide of the invention.

IV. Pharmaceutical Compositions of the Invention

The invention provides pharmaceutical compositions useful for prophylactic or therapeutic treatment of disorders characterized by inadequate or inappropriate stimulation or action of a Fas receptor-mediated pathway caused or mediated by soluble FasL. Such compositions generally comprise an active prophylactic or therapeutic agent (e.g., a polypeptide of the invention, a vector containing a nucleic acid sequence encoding a polypeptide of the invention, or an isolated host cell containing a nucleic acid sequence encoding a polypeptide of the invention, as described above) and a pharmaceutically acceptable carrier. In such compositions, the polypeptide of the invention is typically attached, bound, coupled to, or linked to a cell membrane. Such compositions are useful for parenteral administration, i.e., subcutaneously, intramuscularly and particularly, intravenously, to patients suffering from, or at risk of, conditions or disorders characterized by inadequate or inappropriate stimulation or action of a Fas receptor-mediated pathway, including inappropriate stimulation or action of a Fas receptor-mediated pathway caused or mediated by soluble FasL, in a cell, tissue, or organ of the patient. Such compositions are also useful in the prophylactic or therapeutic treatment of a patient's intolerance to a graft and in protecting an organ or tissue from autoimmune destruction in a patient. Such conditions include autoimmune diseases, lymphoproliferative disorders, transplant rejection (particularly, following heart, lung, kidney or liver transplants), graft vs. host disease (following bone marrow transplants), inflammation, fulminant hepatitis, GVHHD, AIDS, and various forms of cancer, as discussed above.

In one aspect, compositions of the invention comprise a polypeptide having at least 70%, 80%, 85%, or 90% sequence identity with the amino acid sequence of SEQ ID NO:1 (or allelic or species variation or biologically active fragment thereof) and a capacity to activate a Fas receptor-mediated pathway. The amino acid sequence differs from the sequence of SEQ ID NO:1 (or allelic or species variation or biologically active fragment thereof) by at least one mutation within a FasL protease recognition region within SEQ ID NO:1 (or allelic or species variation or biologically active fragment thereof), which comprises an amino acid sequence within SEQ ID NO:1. The mutation inhibits proteolytic cleavage of the polypeptide from a first cell membrane relative to proteolytic cleavage of SEQ ID NO:1 (or allelic or species variation or biologically active fragment thereof) from a second cell membrane.

The form of compositions of the invention depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation also includes other carriers, adjuvants, or nontoxic, nontherapeutic, nonimmunogenic stabilizers and the like.

The compositions for parenteral administration commonly comprise a solution of a polypeptide of the invention dissolved in a pharmaceutically acceptable carrier, preferably an aqueous carrier. A variety of aqueous carriers can be used, e.g., water, buffered water, 0.4% saline, 0.3% glycine and the like. These solutions are sterile and generally free of particulate matter. The compositions can contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate. The concentration of the polypeptides in these formulations can vary widely, and are selected primarily based on fluid volumes, and viscosities in accordance with the particular mode of administration selected.

The agents of this invention can be administered in the form of a depot injection or implant preparation which can be formulated in such a manner as to permit a sustained release of the active ingredient.

Polypeptides of the inventions or compositions containing such polypeptides can be administered for prophylactic and/or therapeutic treatments. In therapeutic applications, polypeptides or compositions thereof are administered to a patient already affected in an amount of polypeptide sufficient to cure or at least partially arrest the condition and its complications. An amount of polypeptide adequate to accomplish this is defined as a "therapeutically effective amount." Amounts effective for this use depend upon the severity of the condition and the general state of the patient's own immune system. Single or multiple administrations on a daily, weekly, or monthly schedule can be carried out with dose levels and pattern being selected by the treating physician.

In prophylactic applications, polypeptides of the invention or compositions containing such polypeptides are administered to a patient who is at risk of developing the disorder or disease state to enhance the patient's resistance. Such an amount of polypeptide is defined to be a "prophylactically effective amount." In such applications, the precise amounts of the polypeptide depend upon the patient's state of health and general level of immunity.

In another aspect, pharmaceutical compositions of the invention comprise polypeptides of the invention as described herein in a pharmaceutically acceptable carrier, such as a liposome or particle to which the polypeptide is coupled, linked, anchored, or attached.

The invention also provides pharmaceutical compositions comprising vectors containing a nucleic acid sequence encoding a polypeptide of the invention, as described above (e.g., SEQ ID NO:2 or an allelic or species variation or biologically active fragment thereof) and a pharmaceutically acceptable carrier. In one aspect, such compositions further comprise lipids complexed with the vector. The vector-lipid particles of the invention may be prepared according to standard techniques and, in one embodiment, further comprise a pharmaceutically acceptable carrier. Generally, normal saline will be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, and globulin. These compositions are usually sterile. Aqueous solutions can be packaged for use or filtered under aseptic conditions and lyophilized, the lyophilized preparation being combined with a sterile aqueous solution prior to administration. The compositions can contain pharmaceutically acceptable auxiliary substances, as required, to approximate physiological conditions, such as pH adjusting and buffering agents, tonicity adjusting agents and the like, for example, sodium acetate, sodium lactate, sodium chloride, potassium chloride, and calcium chloride. Additionally, in one aspect, the particle suspension includes lipid-protective agents which protect lipids against free-radical and lipid-peroxidative damages on storage. Lipophilic free-radical quenchers, such as alphatocopherol and water-soluble iron-specific chelators, such as ferrioxamine, are suitable.

The concentration of vector-lipid particles in the pharmaceutical formulations can vary widely, and will be selected primarily by fluid volumes, viscosities, in accordance with the particular mode of administration selected. The amount of particles administered depends upon the particular label used, the condition, disease state, or disorder being diagnosed and the judgment of the clinician.

V. Organs and Tissues of the Invention

The invention provides an isolated organ or tissue on which a polypeptide of the invention resides, wherein the polypeptide results from expression of a nucleic acid sequence encoding the polypeptide, the nucleic acid sequence is integrated into the genome of cells of the organ or tissue, or replicating autonomously of the genome of the cells, and is expressed. Such polypeptides include those described above.

Such organs and tissues are useful in alleviating symptoms of a patient suffering from a disorder characterized by inadequate or inappropriate stimulation or action of a Fas receptor-mediated pathway, including inappropriate stimulation or action of a Fas receptor-mediated pathway caused or mediated by soluble FasL. Such organs and tissues can be transplanted into individuals suffering from such disorders.

Organs and tissues expressing polypeptides of the invention can be prepared by using a variety of methods, including the methods for modifying the phenotype of cells as described herein. The organ or tissue to be modified can be isolated from the patient suffering from a disorder characterized by inadequate or inappropriate stimulation or action of a Fas receptor-mediated pathway, including inappropriate stimulation or action of a Fas receptor-mediated pathway caused or mediated by soluble FasL. Alternatively, an organ or tissue sample from a tissue/organ donor not suffering from such a disorder can be utilized and modified accordingly, and the cells of the organ or tissue can be isolated. The phenotype of such cells can be modified by contacting the cells with a composition comprising a vector containing a nucleic acid sequence encoding a polypeptide of the invention, as described above, and a pharmaceutically acceptable carrier. For example, an organ or tissue to be transplanted into a patient can be perfused in vivo or ex vivo via the vascular supply with a gene therapy vector (such as adenoviral vectors, retroviral vectors, lentivirus vectors, adenovirus-associated viral vectors, or the like) containing a nucleic acid encoding a polypeptide of the invention, or via "gene gun" techniques prior to transplantation. See, e.g., Tam, *Nature* 356:152–154 (1992); Barry, *Nature* 377:632–635 (1995), both of which are incorporated by reference herein in their entirety for all purposes. With such methods, the nucleic acid sequence integrates into the genome of the cells, or replicates autonomously of the genome of the cells, and is expressed. After modifying the phenotype of the cells, the cells are delivered or administered to the tissue or organ of the patient. The organ or tissue can be subsequently transplanted into the patient using standard transplantation techniques and methods.

VI. Methods of Modifying Cell Phenotype

The invention also provides methods of modifying the phenotype of cells. Such methods comprising contacting a cell with a composition comprising a vector containing a nucleic acid sequence encoding a polypeptide of the invention and a pharmaceutically acceptable carrier such that the phenotype of said cells is modified. In such methods, the nucleic acid sequence integrates into the genome of the cells and is expressed, or replicates autonomously of the genome of the cells and is expressed. The cells are typically from a tissue or an organ of a patient suffering from a disorder characterized by inadequate or inappropriate stimulation or action of a Fas receptor-mediated pathway, including, for example, inappropriate stimulation or action of a Fas receptor-mediated pathway caused or mediated by soluble FasL. The method further comprises reintroducing the cells into the patient after the phenotype of the cells has been modified.

Some such methods further comprise delivering the cells to the tissue or organ of the patient after modifying the phenotype of cells. In this instance, the surface of each such cell displays a ligand, antibody, or receptor that has an affinity for an antigen (such as a Fas antigen) on the surface of the tissue or organ of interest. See, e.g., Georgiou, *Nature Biotech*. 15:29–34 (1997). In some methods, the modified cells are delivered or administered proximately to the tissue or organ of interest. Alternatively, the modified cells are injected proximately or directly to the tissue or organ of interest.

In some such methods, cells from a patient suffering from a disorder characterized by inadequate or inappropriate stimulation or action of a Fas receptor-mediated pathway, including, e.g., inappropriate stimulation or action of a Fas receptor-mediated pathway caused or mediated by soluble FasL, are contacted with such a composition in vivo in the patient.

VII. Therapeutic and Prophylactic Methods of Treatment

The polypeptides, nucleic acids, cells, compositions (as well as organs and tissues expressing such polypeptides) of the present invention are used in therapeutic and prophylactic methods for the treatment of human or non-human mammalian patients. The term "treatment" or "treating a patient" refers to the full spectrum of treatments for a given disorder from which the patient is suffering, including alleviation of one, most, or all symptoms resulting from that disorder, outright cure for the particular disorder, and prevention of the onset of the disorder. In the context of the present invention, such disorders often are characterized in some measure by inappropriate stimulation or action of a Fas receptor-mediated pathway caused or mediated by soluble FasL. By "inappropriate stimulation" or "inappropriate action" of a Fas receptor-mediated pathway caused or mediated by soluble FasL is meant the production and release of soluble FasL (via proteolytic cleavage of membrane-bound FasL) into local or systemic circulation of the patient with potentially undesirable or damaging side effects, including, e.g., widespread, indiscriminate, nonspecific, and/or premature cell, organ, or tissue death, fulminant liver damage, and other deleterious effects caused by the binding of soluble FasL to FasL expressed on such cells, organs, or tissues (including effects described above). Such damaging or undesirable stimulation or action by soluble FasL includes a level of Fas mediated activity that is below, at, or above the level of Fas mediated activity normally occurring in vivo in an undiseased patient. Such damaging or undesirable stimulation or action is generally characterized by the onset of one of the particular disorders described herein.

The polypeptides, nucleic acids, cells, and compositions of the present invention are useful in therapeutic and prophylactic methods for treating disorders where the administration of FasL to a patient would be of general benefit to the patient, but where the administration of soluble FasL results in local or systemic tissue, cell, or organ damage. Because the subject polypeptides and their compositions (and nucleic acids, cells, organs, tissues, or tissue grafts expressing such polypeptides) comprise a noncleavable form of FasL, they can be delivered or administered to specific site(s) within the patient or into the circulatory system with much less risk of widespread and non-specific tissue or organ damage or injury than with soluble FasL. With such polypeptides, the degree and targeting of treatment of disorders resulting from dysfunction of Fas-mediated pathways (e.g., apoptosis) can be selectively modulated in specific cells, tissues, and organs of a patient in need of such treatment.

In another aspect, such disorders are characterized in some measure by dysfunction of Fas-mediated pathways, and include those disorders characterized by either an inadequate or under-stimulation, e.g., persistence of autoreactive B and T cells leading to lymphoproliferative disorders and acceleration of autoimmune disorders, inappropriate stimulation or action by soluble FasL, or over-stimulation of these Fasmediated pathways, resulting in premature cell death, fulminant liver damage, and other deleterious effects.

By "under-stimulation," "inadequate stimulation," or "inadequate action" is meant a level of Fas mediated activity that is below the level of Fas mediated activity normally occurring in vivo. Such under-stimulation is typically characterized by the onset of one of the particular disorders described herein, or, alternatively, by the prevalence or persistence of Fas responding cells within the patient's system that is in excess of normal levels. Over-stimulation of Fas mediated activity is conversely defined.

Treatment of those disorders that are characterized by an under-stimulation of the Fas mediated mechanisms typically involves administration to the patient of those polypeptides of the invention (or cells, organs, or tissues expressing such polypeptides or compositions of such cells or polypeptides) that are characterized by their ability to activate such Fas-mediated mechanisms or activity (e.g., polypeptides comprising a mutated FasL protease recognition region such that cleavage of the mutated FasL polypeptide from the cell membrane is reduced relative to wild-type FasL, as described herein, and their biologically active fragments; polypeptides comprising an extracellular FasL domain that is linked to a cell membrane by a linker between the cell membrane and the domain, as described herein). In this aspect, the polypeptides of the invention (and cells, organs, or tissues expressing such polypeptides) function as an exogenous source of cell membrane-bound FasL which can be used to regulate and stimulate a normal level of Fas-mediated activity, to artificially and selectively modulate apoptosis in specifically targeted cells, tissues, and organs, to confer immune privilege to transplanted organs, to induce allograft specific tolerance to a host, and to treat various cancers.

In a related aspect, the polypeptides of the present invention and their compositions (or cells, organs, or tissues expressing such polypeptides) are also administered to a patient, as described herein, to augment the patient's normal level of Fas mediated activity, despite the fact that such activity does not result from an "understimulation" or "inadequate stimulation" per se. For example, over-activation of the Fas receptor may be desirable in a number of instances, such as in immunosuppression therapies, to reduce the populations of active lymphocytes. This is particularly useful in preventing graft rejection and in treating autoimmune disorders. As will be appreciated, amounts for such therapy must be appropriately titrated to achieve desired results without causing excess tissue damage to the patient, i.e., resulting from systemic apoptotic cell death.

In general, the above-described methods and treatments involve administering an effective amount of the polypeptides of the invention or compositions thereof (or cells, organs, or tissues expressing such polypeptides) sufficient to augment the level of exogenous FasL in the patient's system to achieve normal or near normal Fas-mediated activity. Such polypeptides or compositions (or cells, organs, or tissues expressing such polypeptides) are delivered proximately or directly to a specific bodily site of interest in the patient (e.g., to specific organ, tissue, or cell) by a variety of methods described herein, including by intravascular injection or by injection proximate or directly to the site of interest (i.e., organ, tissue, or cell).

Treatment of those disorders characterized by an over-stimulation of these mechanisms typically involves administration to the patient of those polypeptides or compositions of the invention that are capable of blocking an interaction between the Fas receptor and a patient's endogenous FasL to inhibit or block the interaction of these entities. For example, by administering to a patient an effective amount of an antibody to FasL, e.g., a blocking antibody, one may block association of endogenous FasL with the Fas receptor and thereby reduce the level of Fas-mediated activation.

In one aspect, the invention provides methods of alleviating a symptom of a patient suffering from a disorder characterized by inadequate or inappropriate stimulation or action of a Fas receptor-mediated pathway or inappropriate stimulation or action by soluble FasL in a tissue, cell, or organ of the patient. Such methods comprise delivering to said tissue, cell, or organ of said patient an effective amount of a cell containing a nucleic acid sequence encoding a polypeptide of the invention, as described above. In a particular aspect, such polypeptide has at least 70%, 80%, 85%, or 90% sequence identity with the amino acid sequence of SEQ ID NO:1 (or an allelic or species variation thereof or biologically active fragment thereof) and a capacity to activate a Fas receptor-mediated pathway. Such amino acid sequence differs from the sequence of SEQ ID NO:1 by at least one mutation within the FasL protease recognition region within SEQ ID NO:1, wherein the mutation inhibits proteolytic cleavage of the polypeptide from a cell membrane to which the polypeptide is bound or linked (i.e., first cell membrane) relative to proteolytic cleavage of SEQ ID NO:1 from a cell membrane to which SEQ ID NO:1 is bound (i.e., second cell membrane).

In some such methods, the cell is delivered or administered proximate to a particular tissue, cell, or organ of interest. In many such methods, the cell is delivered via intravascular injection or by injection directly or proximate to the site of therapy (i.e., tissue, cell, or organ of interest). In some methods, the surface of the cell to be delivered or administered has an affinity for the specific tissue, cell, or organ of interest, and, in some instances, the surface of the cell displays an antibody having an affinity for an antigen on the surface of the tissue or organ that. Alternatively, the surface of the cell displays a ligand or receptor having an affinity for a ligand or receptor located or expressed on the surface of the tissue or organ.

Cells expressing polypeptides of the invention, which are to be utilized in such methods, can be prepared by modifying isolated host cells to express a noncleavable form of FasL prior to transplantation into a patient. Cells to be transplanted (such as bone marrow cells, endocrine cells, or other mammalian cells or cell lines) are transduced to express the polypeptide of the invention (i.e., a noncleavable FasL) with standard gene therapy techniques prior to transplantation. Cell lines expressing such polypeptides are selected prior to transplantation via drug resistance marker selection or via immunomagnetic techniques.

In another aspect, the invention provides methods of alleviating a symptom of a patient suffering from a disorder characterized by inadequate or inappropriate stimulation or action of a Fas receptor-mediated pathway, or inappropriate stimulation or action by soluble FasL, in a cell, tissue, or organ of the patient which comprise delivering to the tissue or organ of the patient an effective amount of a polypeptide of the invention, as described above, that is linked to, coupled to, or combined with a pharmaceutically acceptable carrier having an affinity for the cell, tissue or organ of the patient.

In another aspect, the invention provides methods of alleviating a symptom of a patient suffering from a disorder characterized by inadequate or inappropriate stimulation or action of a Fas receptor-mediated pathway, or inappropriate stimulation or action by soluble FasL, in a cell, tissue, or organ of the patient which comprise introducing into the patient an isolated organ or tissue of the invention, as described above, which expresses a polypeptide of the invention. The noncleavable FasL polypeptides of the invention are particularly useful in methods for the prophylactic or therapeutic treatment of disorders characterized by widespread, nonspecific, or premature cell, organ, or tissue death because such polypeptides remain linked or bound to the cell membrane, thereby allowing for a localized or more specifically targeted effect on a Fas receptor (expressed on a cell, tissue or organ) and eliminating damaging and undesirable effects of the cleaved, soluble form of FasL which can circulate throughout a patient's body and produce nonspecific, widespread, and premature cell death.

In some such methods, the polypeptide residing on the isolated organ or tissue results from expression of the nucleic acid sequence encoding the polypeptide, wherein the nucleic acid sequence is integrated into the genome of the cells of the organ or tissue, respectively, or replicates autonomously of the genome of such cells.

The polypeptides of the invention (and cells, organs, or tissues expressing such polypeptides) are also useful in methods for the prophylactic or therapeutic treatment of intolerance to transplanted grafts, organs, or tissues. As noted above, the Fas/FasL apoptosis pathway holds tremendous promise as a modality to confer immune privilege to transplanted organs, or to induce allograft specific tolerance to the host. Expression of noncleavable FasL on allografts or on "carrier" cells of the host can protect the allograft from alloimmune mechanisms. Additionally, FasL can protect against xenograft rejection. FasL minimizes or eliminates the need for non-specific immunosuppression—which is, at present, one of the major morbidities associated with transplantation. Furthermore, FasL is believed to prevent commonly observed episodes of rejection that often severely compromise the function of the graft. The artificial expression of a noncleavable FasL and its administration to a patient in need thereof with allogenic cells may tolerize the animal to the allogenic stimulus and prolong tolerance of a patient's system to a transplanted graft, without the danger of systemic or non-specific local tissue, organ or cell damage resulting from administration of soluble FasL. Thus, polypeptides of the invention (i.e., noncleavable forms of FasL) are useful in effecting transplant-specific tolerance. Notably, polypeptides of the invention do not protect against host damage caused by direct interaction between cells expressing such polypeptides (i.e., noncleavable FasL) and cells expressing the Fas receptor.

In one aspect, the invention provides methods for the prophylactic or therapeutic treatment of intolerance to a graft of a patient comprise delivering to the graft of the patient an effective amount of a polypeptide of the invention, as described above. In such methods, the polypeptide are combined with, linked to, or coupled to a pharmaceutical carrier, as described herein, and/or administered or delivered proximately to the graft. Delivery or administration is accomplished by the various means described above, including, intravascular injection and, in particular, injection proximate or directly to the graft. In addition, the carrier may have a specific affinity for the graft, such that it specifically interacts with, is attracted to, or binds to a surface receptor located or expressed on the surface of the graft.

In another aspect, the invention provides methods for the prophylactic or therapeutic treatment of intolerance to a graft in a patient which comprise delivering to the patient a graft on the surface of which a polypeptide of the invention resides. In such methods, the polypeptide is often produced by expression of a nucleic acid sequence encoding the polypeptide. The nucleic acid sequence has been integrated into the genome of the cells of the graft, or has replicated autonomously of the genome of such cells, and is expressed.

The polypeptides of the invention (and cells, organs, or tissues expressing such polypeptides) are also useful in methods for protecting organs from various autoimmune diseases and autoimmune destruction, in a manner similar to the protection of allografts. Delivery of such polypeptides of the invention (e.g., those comprising noncleavable forms of FasL) with autoantigens is of benefit to tolerize animals to such autoantigens. This approach is also of benefit with other antigens, such as adenovirus. Adenoviral gene therapies often limited by a severe immune response to the virus. The delivery of such polypeptides comprising noncleavable forms of FasL with the adenovirus in order to tolerize the animal to the adenoviral (and specifically transferred gene) products.

In one aspect, the invention provides methods of protecting an organ or tissue from autoimmune destruction in a patient which comprise delivering to the organ or tissue of the patient an effective amount of a polypeptide of the invention. In such methods, the polypeptide has an affinity for the organ or tissue.

Furthermore, the polypeptides of the invention (and cells, organs, or tissues expressing such polypeptides) are useful in methods for the prophylactic and therapeutic treatment of various forms of cancer, including those outlined above. It is known that a number of spontaneous and induced cancers express the Fas receptor. Several studies have shown that delivery of FasL to these cancer cells can effect apoptosis. See, e.g., Kerr et al., *Cancer* 73:2013–2026 (1994), published erratum, *Cancer* 73(12):3108 (1994). Polypeptides of the invention (as noncleavable forms of FasL) are expected to be especially useful in specifically targeting and treating cancers in patients in need of such treatment, by delivering such polypeptides proximately to the cancerous site, without incurring systemic injury as would occur with the delivery of soluble FasL.

In general, the quantities of reagents necessary for effective therapy, also referred to herein as an "effective amount," or "therapeutically effective amount," depend upon many different factors, including means of administration, target site, physiological state of the patient and other medicants administered. Thus, treatment doses will need to be titrated to optimize safety and efficacy. Typically, dosages used in vitro provide useful guidance in the amounts useful for in situ administration of these reagents. Animal testing of effective doses for treatment of particular disorders will provide further predictive indication of human dosage. Generally, therapeutically effective amounts of the polypeptides of the present invention will be from about 0.0001 to about 10 mg/kg, and more usually, from about 0.001 to about 0.1 mg/kg of the host's body weight. Various considerations are described, e.g., in GOODMAN AND GILMAN'S: THE PHARMACOLOGICAL BASIS OF THERAPEUTICS (Gilman et al., eds., 8th ed. 1990), and REMINGTON'S PHARMACEUTICAL SCIENCE, supra. Methods of administration, also discussed in the above references, include, e.g., oral, intravenous, intraperitoneal or intramuscular administration, and local administration, including topical, transdermal diffusion and aerosol administration, for therapeutic, and/or prophylactic treatment. The active agent, i.e., the polypeptide component, will generally be administered in a composition additionally comprising a pharmaceutically acceptable carrier. Suitable pharmaceutically acceptable carriers include water, saline, buffers and other compounds described in, e.g., the Merck Index (Merck and Co., Rahway, N.J.). For some methods of administration, e.g., oral, it is desirable to provide the active ingredient in a liposomal formulation. This is particularly desirable where the active ingredient is subject to degradative environments, for example, proteolytic digestive enzymes. Liposomal formulations are well known in the art, and are discussed in REMINGTON's PHARMACEUTICAL SCIENCE, supra. Administration may also be carried out by way of a controlled release composition or device, whereby a slow release of the active ingredient allows continuous administration over a longer period of time.

Constituents of pharmaceutical compositions of the invention, in addition to the active agents described herein, include those generally known in the art for the various administration methods used. For example, oral forms generally include powders, tablets, pills, capsules, lozenges and liquids. Similarly, intravenous, intraperitoneal or intramuscular formulations will generally be dissolved or suspended in a pharmaceutically acceptable carrier, e.g., water, buffered water, saline, and the like. Additionally, in another aspect, these compositions include additional constituents which may be required to approximate physiological conditions, such as pH adjusting and buffering agents, tonicity adjusting agents, wetting agents and the like. For solid compositions, conventional nontoxic solid carriers may be used which include, e.g., pharmaceutical grades of mannitol, lactose, starch, magnesium stearate, sodium saccharin, talcum, cellulose, glucose, sucrose, magnesium carbonate and the like.

EXAMPLES

Example 1

Design of Deletion Mutants

In the present invention, the proteolytic cleavage site of wild-type human FasL was postulated based on comparisons between the known amino acid sequence of human TNFα and the known amino acid sequence of human FasL. The metalloprotease cleavage site of human TNFα was previously determined precisely by sequencing the terminal amino acids of soluble TNF-α. Kriegler et al., Cell 53:45–53 (1988) (incorporated herein by reference in its entirety for all purposes). The metalloprotease recognition region of amino acids of wild-type human TNFα is shown in FIG. 1. The known cleavage site of human TNFα is indicated in FIG. 1 by a vertical line between amino acid residue 76 (alanine) and amino acid residue 77 (valine). Perez et al., Cell 63:251–258 (1990) (incorporated herein by reference in its entirety for all purposes). In an attempt to create a noncleavable, functional form of TNF-α, Perez et al. generated a family of mutants of the wild-type human TNF gene by deleting, via site-directed mutagenesis, the codons encoding the known TNF cleavage site between two specific amino acid residues of 26-kDa TNF-α, as well as various combinations of flanking amino acids. Id. at 251–254. Deletion mutants lacking both the known cleavage site and various numbers of codons either 5' or 3' to that site were generated. Id. Deletion of 12 codons 3' to the cleavage site was found to encode a noncleavable, functional form of human TNF-α. Id. at 252–253. The 12 amino acid residues that were eliminated by Perez et al. are shown in FIG. 1 in bold type.

In an attempt to generate functional, noncleavable mutants of wild-type FasL, the amino acid sequence of the metalloprotease recognition region of TNF-α was examined and compared with the amino acid sequence of wild-type human FasL. It is well known that proteolytic cleavage of the 40-kDa membrane-bound form of FasL produces a 26-kDa soluble form of FasL. Based on the size of this soluble FasL, as well as sequence comparisons between the cleavage site of TNF-α and the known amino acid sequence of FasL, we focused our attention on a sequence of about 20 amino acids within full-length FasL postulated to contain the proteolytic cleavage site. Briefly, mutant form of wild-type FasL were generated by first preparing mutants of the wild-type human FasL gene. Mutants of the FasL gene were constructed by deleting, via sitedirected mutagenesis, the codons encoding amino acids believed to flank and/or include the postulated metalloprotease cleavage site for FasL as described more fully in Example 2 below. Kayagaki et al., supra; Tanaka et al., EMBO J. 14:1129–1135 (1995). The postulated cleavage site of human FasL is indicated by a vertical line between amino acid residue 126 (serine) and amino acid residue 127 (leucine) of FasL.

Three such amino acid sequence deletions are shown in FIG. 1 in bold type. Deletion mutant 1 ("mutant delta 1") was prepared by deleting the codons encoding amino acid residues 126 to 129 (inclusive) of wild-type (i.e., naturally occurring) human FasL. This deletion of four amino acids was made at the postulated metalloprotease cleavage site based on sequence analysis. Kayagaki et al., supra; Tanaka et al., EMBO J. 14:1129–1135 (1995).

Deletion mutant 2 ("mutant delta 2") was prepared by deleting the codons encoding amino acid residues 126 to 135 (inclusive) of wild-type human FasL as described more fully below. This deleted sequence of 10 amino acids includes the amino acids deleted for deletion mutant 1 and additional amino acids residues extending beyond the homologous metalloprotease cleavage site in TNF-α.

Deletion mutant 3 ("mutant delta 3") was created by deleting the codons encoding amino acid residues 126 to 145 (inclusive) of wild-type human FasL. This deletion of 20 amino acids encompasses the amino acids deleted in deletion mutant 2 and extends to the highly conserved amino acid motif, val-ala-his. The val-ala-his motif also appears to be highly conserved among TNF family members, and deletions made into the val-ala-his motif have been found to eliminate TNF activity. Perez et al., supra.

Example 2

Generation of the Fas Ligand Deletion Mutants

All deletion mutants were created using the inverse polymerase chain reaction method. See Dorrell et al., *Biotechniques* 21:604–606 (1996). The plasmid pBX-hFL1, which contains the cDNA of human FasL in the XbaI site of pBluescript II SK+, was provided by Dr. S. Nagata. See Takahashi et al., *Int'l Immunol.* 6:1567–1574 (1994). Briefly, primers were made with NheI restriction sites (indicated in bold on the primer sequences below) and were designed to amplify the entire plasmid except the portion to be deleted. The primers were as follows:

Deletion Mutant 1
   A) 5'-ACGGCTAGCTGTGTGCATCTGGCTGG
   B) 5'-CAGGCTAGCCAAATAGGCCACCCC
Deletion Mutant 2
   A) 5'-ACGGCTAGCTGTGTGCATCTGGCTGG
   B) 5'-CAGGCTAGCCCACCCCCT-GAAAAA
Deletion Mutant 3
   A) 5'-ACGGCTAGCTGTGTGCATCTGGCTGG
   B) 5'-CAGGCTAGCGTG-GCCCATTTAACAGGC Note that the same primer, designated by the letter "A," was used for the three deletion mutants. PCR was performed with Pfu polymerase for 25 cycles. The PCR product was purified, cut with NheI, ligated, and retransformed into bacteria using standard techniques. The mutants were confirmed by sequencing. The cDNAs were then excised with XbaI and cloned into the XbaI site of the mammalian expression vector pCDNA3.

Example 3

Functional Analysis of Fas Ligand Deletion Mutants

The various constructs of human FasL cDNA (wild-type FasL construct (WT FasL)), deletion mutant 1, deletion mutant 2, and deletion mutant 3 were transfected into COS-7 cells using lipofectamine (Gibco). Approximately 4×10⁵ cells were transfected. Forty-eight hours after transfection, the supernatants were collected and the cells were lightly trypsinized. Such cells were used as effector cells in a cytotoxicity assay. Cells of the human T-lymphoma cell line, Jurkat T cell, which has been shown to express Fas and undergo apoptosis in response to Fas ligation, were loaded with chromium-15 and employed as target cells in the assay. See Alderson et al., *J. Exp. Med.* 181:71–77 (1995) (incorporated herein by reference in its entirety for all purposes). To detect Fas-induced killing, $^{51}$Cr-labelled Jurkat cells were incubated overnight (about 12–16 hours) in 10% fetal calf serum in RPMI with varying numbers of effector cells. $^{51}$Cr content of the supernatants was detected by standard scintillation counting. The data is FIG. 2 reflects at least three such experiments. All assays were run in triplicate. COS-7 cells transfected with a CMV β-galactosidase construct ("Bgal") were used as a negative control.

The results of a typical cytotoxicity assay is shown in FIG. 2. Cell death was measured by the percentage of chromium-51 released from the Jurkat cells due to induced apoptosis and lysis of such cells. Mutant 1 (designated "Del 1"in FIG. 2) exhibited a cell-killing activity equivalent to that of wild-type FasL ("WT FasL"). In contrast, mutants 2 and 3 (designated "Del 2"and "Del 3"in FIG. 2) exhibited a cellkilling activity almost two-fold higher than that of wild-type FasL at lower effector-to-target ("E/T") cell ratios. (Cells expressing FasL constitute effector cells, while cells expressing Fas constitute target cells). Mutant 2 reproducibly reached a plateau level in killing activity at an E/T ratio of 0.11. This level was slightly higher than the maximum killing activity level observed for the wild-type at an E/T ratio of about 1.0. Mutant 3 continued to be approximately two-fold more cytotoxic than wild-type FasL at all E/T ratios. This pattern was observed with two independent plasmid preparations of the constructs. Thus, for these three deletion mutants, functional analysis demonstrated that the mutant from which the most amino acids were deleted (mutant 3) was the most effective in killing Fas-bearing target cells. These results suggested either a higher level of expression or an increased potency for mutant 3.

Example 4

Analysis of Fas Ligand Expression in Deletion Mutants

Expression of FasL in the FasL deletion mutant molecules was determined by standard fluorescence activated cell sorting ("FACS") analysis (Coulter Corp., Hialeah, Fla.). Forty-eight hours after transfection with the various FasL constructs described above, COS-7 cells were lightly trypsinized and stained with a biotinylated monoclonal antibody to human FasL, NOK-1 (Pharmingen, Calif.) for 30 min. Tanaka et al., *EMBO J.* 14:1129–1135 (1995) (incorporated herein by reference in its entirety for all purposes). After two washes, bound antibody was detected using PE-conjugated streptavidin. Cytometric analysis was carried out by using FACS analysis techniques. COS7 cells transfected with a CMV β-galactosidase construct ("Bgal") were employed as a negative control.

The results of a representative experiment are presented in FIG. 3. Approximately twice as many cells stained positively for FasL when transfected with mutants 2 or 3 (i.e., "Del 2"or "Del 3", respectively) as compared with cells transfected with the wild-type human FasL ("WT") or mutant 1 ("Del 1"). This result was not due to differences in transfection efficiency, which was determined by cotransfection with the construct pEF-GFP. pEF-GFP directs the expression of green fluorescent protein ("GFP") under the elongation factor II promoter ("pEF") and can be detected in the FITC gate of the FACS analyzer.

Figure 4:
FIG. 4 shows Western blot analysis of FasL expression of COS-7 cells transfected with wild-type human FasL ("WT") or deletion mutant 3 ("Del 3"). The relative amount of FasL expressed in WT FasL or deletion mutant 3 is shown. Lysates from two separate transfections using different plasmid DNA preparations are shown. A molecular marker is shown on the left. Cell lysates, supernatants, and membrane fractions were prepared as described in the Examples below.

To quantitate differences in protein expression directly, Western blot analysis using an anti-FasL polyclonal antibody (N-20, Santa Cruz Biotech, Calif.) was carried out on cell lysates of COS-7 cells transfected with either wild-type human FasL or mutant 3 FasL ("Del 3"). The cell lysate was prepared according to the manufacturer's instructions. 12.5 μl of the cell lysate was mixed with an equal volume of 2× reducing SDS-PAGE sample buffer, boiled for 3 minutes, and run on a 12% polyacrylamide gel. After electrophoretic transfer to nitrocellulose membranes, the blot was incubated with a 1:100 dilution of N-20, followed by a peroxidase coupled anti-rabbit antibody (Amersham). The proteins were visualized by enhanced chemiluminescence (Amersham). As shown in FIG. 4, in two separate transfections, COS7 cells transfected with mutant 3 FasL ("Del 3") displayed an approximately two-fold higher level of FasL expression than did COS-7 cells transfected with the wild-type FasL ("WT"). This increased expression results in a higher level of cytotoxicity to Fasbearing target cells.

Example 5

Detection of Soluble Fas Ligand

To detect the amount of soluble (i.e., secretory) FasL released from the transmembrane form of FasL by proteolytic cleavage, COS-7 cells transfected with various constructs (i.e., wild-type FasL, mutant 1, mutant 2, or mutant 3) were labeled with $^{35}$S-methionine. The supernatants of the radiolabelled cells were collected and spun at 70,000×g for 1 hour to remove cellular debris. The resulting supernatants were incubated overnight at 4° C. with biotinylated NOK-1 antibody coupled to streptavidincoated magnetic bead. The beads were then washed 5 times with immunoprecipitation buffer. Next, the beads were boiled in SDS-PAGE sample buffer for 3 minutes and the samples were analyzed by SDS-PAGE on a 12% acrylamide gel. The dried gel was subjected to autoradiography.

Figure 5:
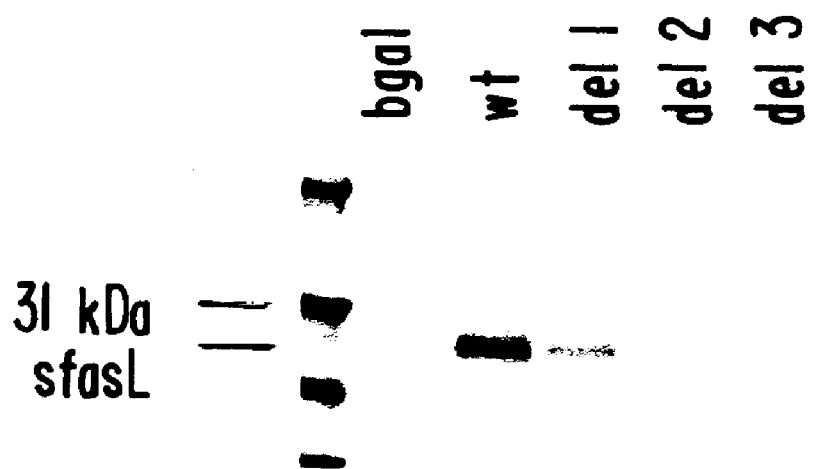
FIG. 5 shows an autoradiograph which demonstrates the detection of soluble FasL in supernatants of COS-7 cells transfected with wild-type human FasL ("WT"), deletion mutant 1 ("Del 1"), deletion mutant 2 ("Del 2"), or deletion mutant 3 ("Del 3") by immunoprecipitation, as described in the Examples below. A molecular marker is shown on the left. COS-7 cells transfected with a β-galactosidase construct ("Bgal") were used as a negative control.

As shown in FIG. 5, the amount of soluble FasL found in the supernatant of mutant 1 ("Del 1") was slightly less than that found in the supernatant of wild-type FasL ("WT"). Very little soluble FasL was observed in the supernatant of mutant 2 ("Del 2"), as compared with the supernatant of wild-type FasL. Significantly, no soluble FasL was observed in the supernatant of mutant 3 FasL ("Del 3"), even after exposing film to the membranes for prolonged time periods. Based on these results, it appears that mutant 3 does not release a soluble (i.e., secretory) form of FasL released from the transmembrane form of FasL by proteolytic cleavage and thus that mutant 3 constitutes a noncleavable form of FasL.

Example 6

Cytotoxicity of Supernatants From Wild-Type and Noncleavable Mutant Expressing Cells The cytotoxic effects of mutant 3 FasL were determined as follows. COS-7 cells were transfected with either wild-type FasL or mutant 3 expression constructs. Twenty-four (24) hours after transfection, normal COS-7 medium (10% fetal calf serum ("FCS") in Dulbecco's modified Eagle's medium ("DMEM")) was replaced with reduced serum medium (1% FCS in DMEM). After an additional forty-eight (48) hours, the respective supernatants for both the wild-type FasL and mutant 3 expression constructs were collected and spun at 70,000×g for 1 hour to remove cellular debris. A total of eight (8) serial (3-fold) dilutions of the resulting supernatant were made. Each dilution comprised a three-fold dilution of the preceding supernatant. See, e.g., Kayagaki et al., supra.

Cells of the Fas-sensitive cell line W4 (a WR19L lymphoma cell line stably transfected with a Fas expression construct) ("W4 cells") were chosen as target cells for FasL present in the supernatants because such cells express the Fas antigen. The W4 cells were labeled with chromium-51 and were then placed in a particular supernatant.

Figure 6:
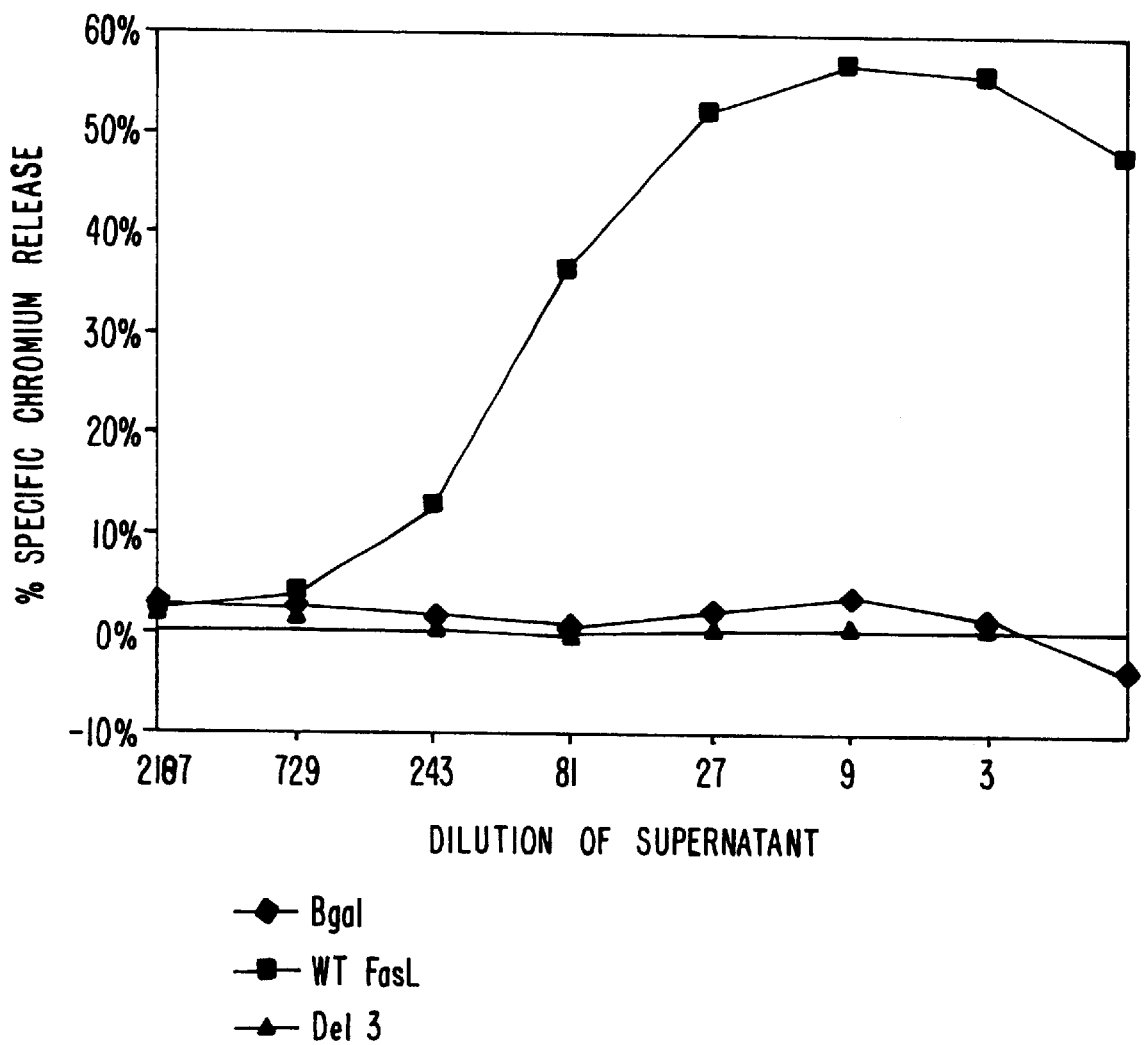
FIG. 6 shows an assay demonstrating the cytotoxicity of the supernatant of COS-7 cells transfected with wild-type ("WT") FasL construct (—■—) or deletion mutant ("Del 3") (—▲—), as described in the Examples below. Supernatant from COS-7 cells transfected with a β-galactosidase construct ("Bgal") (—♦—) served as a negative control. Cells of the Fas ligand sensitive cell line W4 (WR19L lymphoma cell line stably transfected with a Fas expression construct), which expresses Fas, were labelled with $^{51}$Cr and placed in serial dilutions of the cell culture supernatants. The [$^{51}$Cr]-labelled cells served as target cells for WT FasL and deletion mutant 3 ("Del 3"). Results are expressed as percentage of $^{51}$Cr released versus serial (3-fold) dilutions of the cell culture supernatant. Cell death and the degree of apoptosis induced by the various mutant constructs are reflected by the relative percentage of $^{51}$Cr released from the Jurkat cells due to lysis of such cells. Cell culture supernatants from WT FasL expressing cells exhibited high levels of cytotoxicity to W4 Fas expressing cells, as is reflected by the relative percentage of $^{51}$Cr released from such cells due to lysis of such cells. Cell culture supernatants from cells expressing deletion mutant 3 or from control cells transfected with a β-galactosidase construct ("Bgal") showed no toxicity.

After sixteen (16) hours, the amount of released $^{51}$Cr from the target cells was assayed to measure cell death. The results of this assay, which are presented in FIG. 6, are expressed as a relative percentage of $^{51}$Cr released versus relative dilution of the supernatant from COS-7 cells transfected with WT FasL or mutant 3 ("Del 3") As shown in FIG. 6, a number of the (diluted) supernatants from wild-type FasL expressing cells exhibited high levels of cytotoxicity toward W4 cells, as is reflected by the relatively large percentage of $^{51}$Cr released from such cells due to lysis of such cells (see e.g., the effects of supernatants having been prepared by making 1-, 3-, 9-, 27-, 81-, and 243-fold dilutions of the original supernatant from WT FasL expressing cells).

In contrast, none of the supernatants comprising serial dilutions of the original supernatant from either mutant 3 or from control cells transfected with a β-galactosidase ("Bgal") construct showed any cytotoxicity toward W4 cells. These results demonstrate that the mutant 3 form of FasL does not release a soluble or secretory FasL into the supernatant into which the FasL expressing cell is placed. Rather, mutant 3 comprises a functional, noncleavable form of FasL which exhibits a high degree of cytotoxicity toward Fas expressing cells by inducing apoptosis in such cells.

Because Fas-mediated apoptosis has been shown to be especially potent in hepatocytes, the cytotoxicity of the supernatants from COS-7 cells transfected with WT FasL or mutant 3 was also tested on isolated rat hepatocytes in vitro. Previous studies have demonstrated that mice injected with anti-Fas antibodies die rapidly from liver failure as a result of massive hepatocyte apoptosis. See, e.g., Ogasawara et al., supra. Primary isolated hepatocytes, however, require the addition of cycloheximide or actinomycin D in order to undergo apoptosis readily in response to anti-Fas antibodies. Ni et al., supra. The cytotoxic effects of supernatants resulting from incubation with mutant 3 FasL was on isolated rat hepatocytes were studied as follows.

Primary rat hepatocytes were plated onto flat-bottom, 96-well plates coated with collagen type I immediately after isolation. After a period of twenty-four (24) hours, the wells were washed to remove nonadherent, nonviable cells. Supernatants from transfected COS-7 cells were then added to the wells in varying dilutions (dilution factors of 1:4 and 1:16), with or without the addition of cycloheximide at 50 μg/ml or actinomycin D at 0.05 μg/ml. See Ni et al., supra. Cycloheximide was used to augment FasL mediated cytotoxicity as previously described in Ni et al., supra.

Figure 7A:
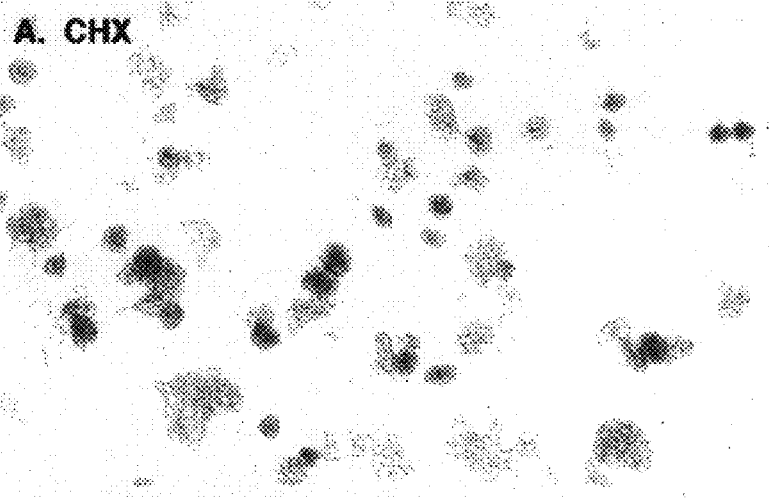
FIG. 7 shows the cytotoxic effects of cell culture supernatants (dilution 1:4) from COS-7 cells transfected with either wild-type ("WT") FasL and deletion mutant 3 on isolated primary rat hepatocytes in vitro as assessed by trypan blue exclusion, as described in detail below. Cycloheximide ("CHX") was used to augment FasL mediated cytotoxicity as previously described in Ni et al., *Exp. Cell Res.* 215:332–337 (1994). Supernatants from wild-type FasL with cycloheximide ("WT+CHX") induced dramatic hepatocyte death (Panel B), while supernatants from mutant 3 ("Del 3") with cycloheximide alone (Panel C) showed no increased hepatocyte death compared to background with cycloheximide alone (CHX) (Panel A).
Figure 7B:
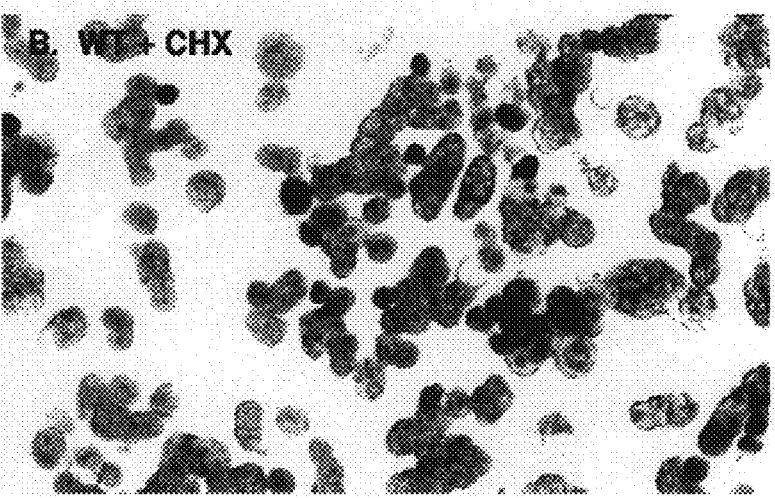
Figure 7C:
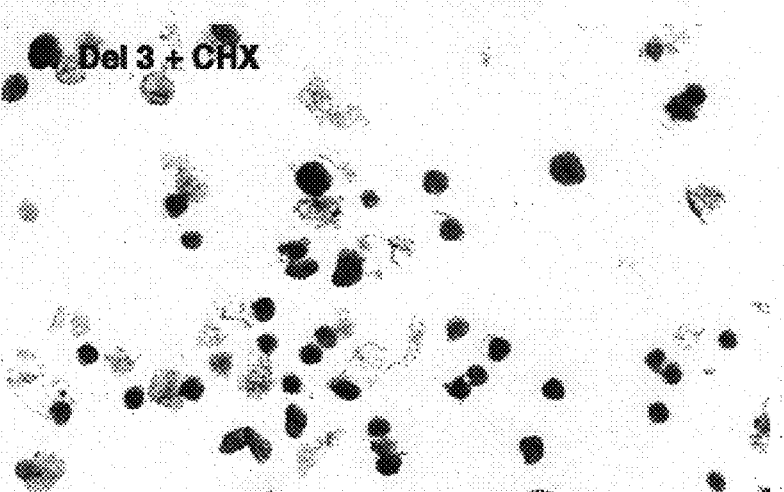

After sixteen (16) hours, the hepatocytes were stained for viability with trypan blue according to commonly known techniques. See, e.g., CURRENT METHODS IN IMMUNOLOGY (Wiley Publishers). As shown in FIG. 7, supernatants (dilution factor 1:4) from wild-type FasL with cycloheximide induced dramatic hepatocyte death (Panel B). Supernatants from mutant 3 with cycloheximide alone (Panel C) showed no increased hepatocyte death compared to background (cycloheximide alone, Panel A). A nonspecific hepatocyte death rate of approximately 20% in untreated overnight cultures was observed. This percentage is within the norm for primary rat hepatocyte. Cycloheximide alone had no effect on this nonspecific cell death. Similar results were seen using actinomycin D (not shown).

While the foregoing invention has been described in some detail for purposes of clarity and understanding, it will be clear to one skilled in the art from a reading of this disclosure that various changes in form and detail can be made without departing from the true scope of the invention. The above examples are provided to illustrate the invention, but not to limit its scope; other variants of the invention will be readily apparent to those of ordinary skill in the and are encompassed by the claims of the invention. The scope of the invention should, therefore, be determined not with reference to the above description, but instead should be determined with reference to the appended claims along with their full scope of equivalents. All publications and patent documents cited in this application are incorporated herein by reference in their entirety for all purposes to the same extent as if each individual publication or patent document were so individually denoted.

What is claimed is:

1. An isolated polypeptide having at least 80% sequence identity with the amino acid sequence of SEQ ID NO:1 and a capacity to activate a Fas receptor-mediated pathway, said amino acid sequence differing from the sequence of SEQ ID NO:1 by at least one mutation within a Fas ligand (FasL) protease recognition region within SEQ ID NO:1, said FasL protease recognition region comprising an amino acid sequence within SEQ ID NO:1, whereby under conditions that would result in cleavage of FasL from a cell, the mutation inhibits proteolytic cleavage of the polypeptide from a cell membrane under conditions which would result in proteolytic cleavage of a polypeptide having an amino acid sequence of SEQ ID NO:1 from a cell membrane.

2. The polypeptide of claim 1, wherein the polypeptide is a full-length Fas ligand.

3. The polypeptide of claim 1, wherein said Fas receptor-mediated pathway is apoptosis.

4. The polypeptide of claim 1, wherein said polypeptide is expressed on the surface of a cell.

5. The polypeptide of claim 1, wherein the mutation comprises:

deletion of at least one amino acid residue from the amino acid sequence of the FasL protease recognition region of SEQ ID NO:1;

substitution of at least one amino acid residue in the amino acid sequence of the FasL protease recognition region of SEQ ID NO:1;

insertion of at least one additional amino acid residue into the amino acid sequence of the FasL protease recognition region of SEQ ID NO:1; or any combination thereof.

6. The polypeptide of claim 1, wherein the mutation comprises deletion of amino acid residue 126 to amino acid residue 135 of SEQ ID NO:1.

7. The polypeptide of claim 1, wherein the mutation comprises deletion of amino acid residue 126 to amino acid residue 145 of SEQ ID NO:1.

8. A pharmaceutical composition comprising the polypeptide of claim 1 in a pharmaceutically acceptable carrier.

9. The pharmaceutical composition of claim 8, wherein the carrier is a liposome.

10. A composition comprising a vector comprising a nucleic acid sequence encoding the polypeptide of claim 1 and a pharmaceutically acceptable carrier.

11. The composition of claim 10, further comprising lipids complexed with the vector.

12. An isolated nucleic acid sequence encoding a polypeptide of claim 1.

13. A vector comprising a nucleic acid sequence of claim 12.

14. An isolated host cell containing a nucleic acid sequence of claim 12.

15. The cell of claim 14, wherein said cell is a mammalian cell.

16. The cell of claim 14, wherein the polypeptide is expressed on the surface of said cell.

17. The polypeptide of claim 1, wherein the mutation is deletion mutant 1 (SEQ ID NO:3), or fragment thereof.

18. The polypeptide of claim 1, wherein the mutation is deletion mutant 2 (SEQ ID NO:4), or fragment thereof.

19. The polypeptide of claim 1, wherein the mutation is deletion mutant 3 (SEQ ID NO:5), or fragment thereof.

20. The polypeptide of claim 1, wherein the mutation is deletion mutant 1 (SEQ ID NO:3) or a variant thereof that is at least 95% identical to SEQ ID NO:3, and wherein under conditions that would result in cleavage of Fas ligand (FasL) having SEQ ID NO:1 from a cell, said polypeptide is not cleaved.

21. The polypeptide of claim 1, wherein the mutation is deletion mutant 2 (SEQ ID NO:4) or a variant thereof that is at least 95% identical to SEQ ID NO:4, and wherein under conditions that would result in cleavage of Fas ligand (FasL) having SEQ ID NO:1 from a cell, said polypeptide is not cleaved.

22. The polypeptide of claim 1, wherein the mutation is deletion mutant 3 (SEQ ID NO:5) or a variant thereof that is at least 95% identical to SEQ ID NO:5, and wherein under conditions that would result in cleavage of Fas ligand (FasL) having SEQ ID NO:1 from a cell, said polypeptide is not cleaved.

23. An isolated polypeptide having at least 80% sequence identity with the amino acid sequence of SEQ ID NO:1 and a capacity to activate a Fas receptor-mediated pathway, said amino acid sequence differing from the sequence of SEQ ID NO:1 by at least one mutation within a Fas ligand (FasL) protease recognition region within SEQ ID NO:1, wherein under conditions that would result in cleavage of FasL having SEQ ID NO:1 from a cell, the mutation inhibits proteolytic cleavage of the polypeptide from a cell membrane relative to proteolytic cleavage of a polypeptide having an amino acid sequence of SEQ ID NO:1 from a cell membrane comprising the polypeptide having an amino acid sequence of SEQ ID NO:1.

24. An isolated polypeptide comprising an extracellular domain of a Fas ligand (FasL), said domain having a capacity to activate a Fas receptor-mediated pathway, wherein said polypeptide is linked to a cell membrane by a linker between said domain and the cell membrane, such that on cleavage of FasL with a protease, said domain remains linked to the cell membrane and under conditions that would result in cleavage of FasL having SEQ ID NO:1 from a cell, Fas ligand is not cleaved.

25. The polypeptide of claim 24, wherein said polypeptide comprises at least 80% sequence identity with the sequence shown in SEQ ID NO:1, or a fragment thereof.

* * * * *

SEQUENCE LISTING

<160> NUMBER OF SEQ ID NOS: 12

<210> SEQ ID NO 1
<211> LENGTH: 281
<212> TYPE: PRT
<213> ORGANISM: Homo sapiens
<220> FEATURE:
<221> NAME/KEY: DOMAIN
<222> LOCATION: (103)..(281)
<223> OTHER INFORMATION: extracellular domain
<220> FEATURE:
<221> NAME/KEY: PEPTIDE
<222> LOCATION: (119)..(154)
<223> OTHER INFORMATION: metalloprotease recognition region
<220> FEATURE:
<223> OTHER INFORMATION: human wild-type Fas ligand (FasL)

<400> SEQUENCE: 1

Met Gln Gln Pro Phe Asn Tyr Pro Tyr Pro Gln Ile Tyr Trp Val Asp
 1               5                  10                  15

Ser Ser Ala Ser Ser Pro Trp Ala Pro Pro Gly Thr Val Leu Pro Cys
            20                  25                  30

Pro Thr Ser Val Pro Arg Arg Pro Gly Gln Arg Arg Pro Pro Pro Pro
        35                  40                  45

Pro Pro Pro Pro Pro Leu Pro Pro Pro Pro Pro Pro Pro Pro Leu Pro
    50                  55                  60

Pro Leu Pro Leu Pro Pro Leu Lys Lys Arg Gly Asn His Ser Thr Gly
65                  70                  75                  80

Leu Cys Leu Leu Val Met Phe Phe Met Val Leu Val Ala Leu Val Gly
                85                  90                  95

Leu Gly Leu Gly Met Phe Gln Leu Phe His Leu Gln Lys Glu Leu Ala
            100                 105                 110

Glu Leu Arg Glu Ser Thr Ser Gln Met His Thr Ala Ser Ser Leu Glu
        115                 120                 125

Lys Gln Ile Gly His Pro Ser Pro Pro Pro Glu Lys Lys Glu Leu Arg
    130                 135                 140

Lys Val Ala His Leu Thr Gly Lys Ser Asn Ser Arg Ser Met Pro Leu
145                 150                 155                 160

Glu Trp Glu Asp Thr Tyr Gly Ile Val Leu Leu Ser Gly Val Lys Tyr
                165                 170                 175

Lys Lys Gly Gly Leu Val Ile Asn Glu Thr Gly Leu Tyr Phe Val Tyr
            180                 185                 190

Ser Lys Val Tyr Phe Arg Gly Gln Ser Cys Asn Asn Leu Pro Leu Ser
        195                 200                 205

His Lys Val Tyr Met Arg Asn Ser Lys Tyr Pro Gln Asp Leu Val Met
    210                 215                 220

Met Glu Gly Lys Met Met Ser Tyr Cys Thr Thr Gly Gln Met Trp Ala
225                 230                 235                 240

Arg Ser Ser Tyr Leu Gly Ala Val Phe Asn Leu Thr Ser Ala Asp His
                245                 250                 255

Leu Tyr Val Asn Val Ser Glu Leu Ser Leu Val Asn Phe Glu Glu Ser
            260                 265                 270

Gln Thr Phe Phe Gly Leu Tyr Lys Leu
        275                 280

<210> SEQ ID NO 2
<211> LENGTH: 843

-continued

```
<212> TYPE: DNA
<213> ORGANISM: Homo sapiens
<220> FEATURE:
<223> OTHER INFORMATION: human wild-type Fas ligand (FasL)

<400> SEQUENCE: 2
atgcagcagc ccttcaatta cccatatccc cagatctact gggtggacag cagtgccagc      60
tctccctggg cccctccagg cacagttctt ccctgtccaa cctctgtgcc cagaaggcct     120
ggtcaaagga ggccaccacc accaccgcca ccgccaccac taccacctcc gccgccgccg     180
ccaccactgc ctccactacc gctgccaccc tgaagaaga gagggaacca cagcacaggc      240
ctgtgtctcc ttgtgatgtt tttcatggtt ctggttgcct tggtaggatt gggcctgggg    300
atgtttcagc tcttccacct acagaaggag ctggcagaac tccgagagtc taccagccag    360
atgcacacag catcatcttt ggagaagcaa ataggccacc ccagtccacc ccctgaaaaa    420
aaggagctga ggaaagtggc ccatttaaca ggcaagtcca actcaaggtc catgcctctg    480
gaatgggaag acacctatgg aattgtcctg ctttctggag tgaagtataa gaagggtggc    540
cttgtgatca atgaaactgg gctgtacttt gtatattcca agtatactt ccggggtcaa      600 tcttgcaaca acctgcccct gagccacaag gtctacatga ggaactctaa gtatcccag     660 gatctggtga tgatggaggg gaagatgatg agctactgca ctactgggca gatgtgggcc    720
cgcagcagct acctgggggc agtgttcaat cttaccagtg ctgatcattt atatgtcaac    780
gtatctgagc tctctctggt caattttgag gaatctcaga cgttttttcgg cttatataag   840 ctc                                                                   843

<210> SEQ ID NO 3
<211> LENGTH: 34
<212> TYPE: PRT
<213> ORGANISM: Homo sapiens
<220> FEATURE:
<221> NAME/KEY: PEPTIDE
<222> LOCATION: (1)..(34)
<223> OTHER INFORMATION: human TNF-alpha metalloprotease recognition
      region (amino acid positions 64-97)

<400> SEQUENCE: 3

Pro Arg Asp Leu Ser Leu Ile Ser Pro Leu Ala Gln Ala Val Arg Ser
 1               5                  10                  15

Ser Ser Arg Thr Pro Ser Asp Lys Pro Val Ala His Val Val Ala Asn
            20                  25                  30

Pro Gln

<210> SEQ ID NO 4
<211> LENGTH: 36
<212> TYPE: PRT
<213> ORGANISM: Homo sapiens
<220> FEATURE:
<223> OTHER INFORMATION: human wild-type FasL metalloprotease
      recognition region (amino acid positions 119-154)

<400> SEQUENCE: 4

Ser Gln Met His Thr Ala Ser Ser Leu Glu Lys Gln Ile Gly His Pro
 1               5                  10                  15

Ser Pro Pro Glu Lys Lys Glu Leu Arg Lys Val Ala His Leu Thr
            20                  25                  30

Gly Lys Ser Asn
        35
```

```
<210> SEQ ID NO 5
<211> LENGTH: 32
<212> TYPE: PRT
<213> ORGANISM: Artificial Sequence
<220> FEATURE:
<223> OTHER INFORMATION: Description of Artificial Sequence:Deletion
      mutant 1 (mutant delta 1) human FasL (amino acids 119-154) with
      amino acids 126-129 deleted

<400> SEQUENCE: 5

Ser Gln Met His Thr Ala Ser Gln Ile Gly His Pro Ser Pro Pro Pro
 1               5                  10                  15

Glu Lys Lys Glu Leu Arg Lys Val Ala His Leu Thr Gly Lys Ser Asn
            20                  25                  30

<210> SEQ ID NO 6
<211> LENGTH: 26
<212> TYPE: PRT
<213> ORGANISM: Artificial Sequence
<220> FEATURE:
<223> OTHER INFORMATION: Description of Artificial Sequence:deletion
      mutant 2 (mutant delta 2) human FasL (amino acid positions
      119-154) with amino acids 126-135 deleted

<400> SEQUENCE: 6

Ser Gln Met His Thr Ala Ser Pro Pro Pro Glu Lys Lys Glu Leu Arg
 1               5                  10                  15

Lys Val Ala His Leu Thr Gly Lys Ser Asn
            20                  25

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence:deletion
      mutant 3 (mutant delta 3) human FasL (amino acid positions
      119-154) with amino acids 126-145 deleted

<400> SEQUENCE: 7

Ser Gln Met His Thr Ala Ser Val Ala His Leu Thr Gly Lys Ser Asn
 1               5                  10                  15

<210> SEQ ID NO 8
<211> LENGTH: 22
<212> TYPE: PRT
<213> ORGANISM: Artificial Sequence
<220> FEATURE:
<223> OTHER INFORMATION: Description of Artificial Sequence:deletion
      mutant of human TNF-alpha (amino acid positions 64-97) with amino
      acids 77-89 deleted for noncleavable functional form

<400> SEQUENCE: 8

Pro Arg Asp Leu Ser Leu Ile Ser Pro Leu Ala Gln Ala Val Ala His
 1               5                  10                  15

Val Val Ala Asn Pro Gln
            20

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence:primer A for
      deletion mutants 1, 2 and 3

<400> SEQUENCE: 9
```

-continued

```
acggctagct tgtgtgcatc tggctgg                                              27

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence:primer B for
      deletion mutant 1

<400> SEQUENCE: 10
caggctagcc aaataggcca cccc                                                 24

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence:primer B for
      deletion mutant 2

<400> SEQUENCE: 11
caggctagcc caccccctga aaaa                                                 24

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence:primer B for
      deletion mutant 3

<400> SEQUENCE: 12
caggctagcg tggcccattt aacaggc                                              27
```